United States Patent
Rondeau

(10) Patent No.: US 6,712,861 B2
(45) Date of Patent: Mar. 30, 2004

(54) COMPOSITION FOR DYEING KERATIN FIBERS AND DYEING METHOD USING SAME

(75) Inventor: Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/331,252

(22) PCT Filed: Oct. 7, 1998

(86) PCT No.: PCT/FR98/02145

§ 371 (c)(1), (2), (4) Date: Aug. 16, 1999

(87) PCT Pub. No.: WO99/20235

PCT Pub. Date: Apr. 29, 1999

(65) Prior Publication Data

US 2003/0000023 A9 Jan. 2, 2003

(30) Foreign Application Priority Data

Oct. 22, 1997 (FR) .............................................. 97/13240

(51) Int. Cl.$^7$ ................................................. A61K 7/13
(52) U.S. Cl. ....................... 8/414; 8/405; 8/407; 8/408; 8/415; 8/426
(58) Field of Search ........................... 8/405, 407, 408, 8/414, 415, 426

(56) References Cited

U.S. PATENT DOCUMENTS

| 3,578,386 A | * | 5/1971 | Kalopissis et al. | 8/426 |
|---|---|---|---|---|
| 3,632,290 A | * | 1/1972 | Tucker et al. | 8/426 |
| 3,955,918 A | * | 5/1976 | Lang | 8/426 |
| 3,985,499 A | | 10/1976 | Lang et al. | 8/426 |
| 4,025,301 A | | 5/1977 | Lang | 8/405 |
| 4,391,603 A | * | 7/1983 | Rosenbaum et al. | 8/424 |
| 4,511,360 A | * | 4/1985 | Monnais et al. | 8/415 |
| 4,657,556 A | * | 4/1987 | Sebag et al. | 8/405 |
| 4,961,925 A | * | 10/1990 | Tsujino et al. | 8/406 |
| 4,964,874 A | * | 10/1990 | Saphakkul | 8/429 |
| 5,078,748 A | * | 1/1992 | Akram et al. | 8/405 |
| 5,314,505 A | * | 5/1994 | Chan et al. | 8/426 |
| 5,520,707 A | * | 5/1996 | Lim et al. | 8/426 |
| 5,865,855 A | * | 2/1999 | Doehling et al. | 8/409 |
| 5,879,412 A | * | 3/1999 | Rondeau et al. | 8/426 |
| 5,919,273 A | * | 7/1999 | Rondeau et al. | 8/412 |
| 5,993,490 A | * | 11/1999 | Rondeau et al. | 8/426 |
| 6,001,135 A | * | 12/1999 | Rondeau et al. | 8/407 |

FOREIGN PATENT DOCUMENTS

| EP | 0 714 954 | 6/1996 |
|---|---|---|
| WO | WO 95/01772 | 1/1995 |
| WO | WO 95/15144 | 6/1995 |

OTHER PUBLICATIONS

English language Derwent Abstract for EP 0 714 954, Jun. 1996.

\* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

The invention relates to a ready-to-use composition for dyeing keratin fibers, and in particular human keratin fibers such as the hair, comprising, in a medium which is suitable for dyeing, at least one suitably selected cationic direct dye and at least one nitrobenzene direct dye, as well as to the dyeing process using this composition.

33 Claims, No Drawings

COMPOSITION FOR DYEING KERATIN FIBERS AND DYEING METHOD USING SAME

The invention relates to a composition for dyeing keratin fibres, and in particular human keratin fibres such as the hair, comprising, in a medium which is suitable for dyeing, at least one suitably selected cationic direct dye and at least one nitrobenzene direct dye, as well as to the dyeing process using this composition.

It is well known to dye keratin fibres, and in particular human hair, with dye compositions containing direct dyes and in particular nitrobenzene direct dyes. However, direct dyes have the drawback, when they are incorporated into dye compositions, of leading to colorations which have insufficient staying power, in particular with regard to shampooing.

The Applicant has now discovered that it is possible to obtain novel dyes capable of leading to intense, unselective colorations which show good resistance to the various attacking factors to which the hair may be subjected, by combining at least one suitably selected cationic direct dye and at least one nitrobenzene direct dye.

This discovery forms the basis of the present invention.

A first subject of the invention is thus a ready-to-use composition for dyeing keratin fibres, and in particular human keratin fibres such as the hair, characterized in that it comprises, in a medium which is suitable for dyeing:

at least one cationic direct dye chosen from:

a) the compounds of formula (I) below:

$$A-D=D-\text{(phenyl)}-N(R_1)(R_2) \quad X^- \quad (I)$$

in which:

D represents a nitrogen atom or a —CH group, $R_1$ and $R_2$, which may be identical or different, represent a hydrogen atom; a $C_1$–$C_4$ alkyl radical which can be substituted with a —CN, —OH or —NH$_2$ radical; or form, with a carbon atom of the benzene ring, an optionally oxygenated or nitrogenous heterocycle which can be substituted with one or more $C_1$–$C_4$ alkyl radicals; a 4'-aminophenyl radical, $R_3$ and $R'_3$, which may be identical or different, represent a hydrogen or halogen atom chosen from chlorine, bromine, iodine and fluorine, or a cyano, $C_1$–$C_4$ alkoxy or acetyloxy radical, $X^-$ represents an anion preferably chosen from chloride, methyl sulphate and acetate, A represents a group chosen by structures A1 to A19 below:

-continued

A12 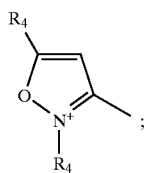

A13 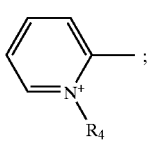

A14 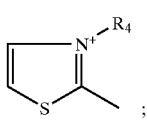

A15 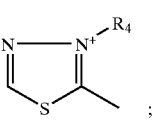

A16 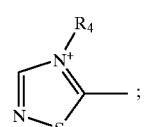

A17 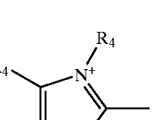

A18 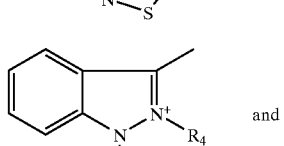 and

A19 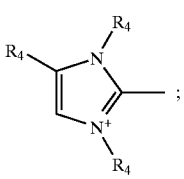

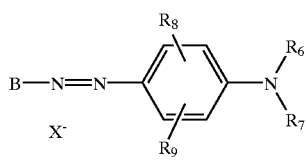

in which $R_4$ represents a $C_1$–$C_4$ alkyl radical which can be substituted with a hydroxyl radical and $R_5$ represents a $C_1$–$C_4$ alkoxy radical, with the proviso that when D represents —CH, when A represents $A_4$ or $A_{13}$ and when $R_3$ is other than an alkoxy radical, then $R_1$ and $R_2$ do not simultaneously denote a hydrogen atom;

b) the compounds of formula (II) below:

(II)

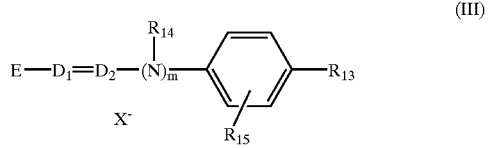

in which:
$R_6$ represents a hydrogen atom or a $C_1$–$C_4$ alkyl radical,
$R_7$ represents a hydrogen atom, an alkyl radical which can be substituted with a —CN radical or with an amino group, a 4′-aminophenyl radical, or forms, with $R_6$, an optionally oxygenated and/or nitrogenous heterocycle which can be substituted with a $C_1$–$C_4$ alkyl radical, $R_8$ and $R_9$, which may be identical or different, represent a hydrogen atom, a halogen atom such as bromine, chlorine, iodine or fluorine, a $C_1$–$C_4$ alkyl or $C_1$–$C_4$ alkoxy radical or a —CN radical, $X^-$ represents an anion preferably chosen from chloride, methyl sulphate and acetate, B represents a group chosen by structures B1 to B6 below:

B1 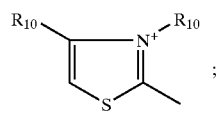

B2 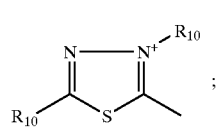

B3 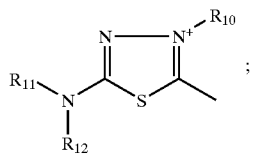

B4 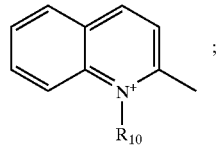

B5 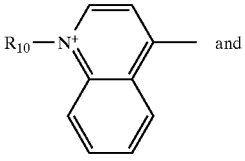 and

B6 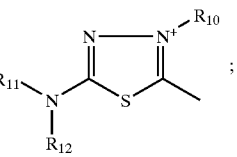

in which $R_{10}$ represents a $C_1$–$C_4$ alkyl radical, $R_{11}$ and $R_{12}$, which may be identical or different, represent a hydrogen atom or a $C_1$–$C_4$ alkyl radical;

c) the compounds of formulae (III) and (III′) below:

(III)

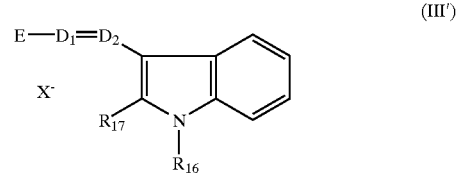

(III′)

in which:
$R_{13}$ represents a hydrogen atom, a $C_1$–$C_4$ alkoxy radical, a halogen atom such as bromine, chlorine, iodine or fluorine or an amino radical, $R_{14}$ represents a hydrogen atom, a $C_1$–$C_4$ alkyl radical, or forms, with a carbon atom of the benzene ring, a heterocycle which is optionally oxygenated and/or substituted with one or more $C_1$–$C_4$ alkyl groups, $R_{15}$ represents a hydrogen or halogen atom such as bromine, chlorine, iodine or fluorine, $R_{16}$ and $R_{17}$, which may be identical or different, represent a hydrogen atom or a $C_1$–$C_4$ alkyl radical, $D_1$ and $D_2$, which may be identical or different, represent a nitrogen atom or a —CH group, m=0 or 1, it being understood that when $R_{13}$ represents an unsubstituted amino group, then $D_1$ and $D_2$ simultaneously represent a —CH group and m=0, $X^-$ represents an anion preferably chosen from chloride, methyl sulphate and acetate, E represents a group chosen by structures E1 to E8 below:

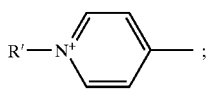
E1

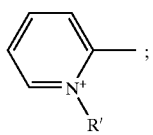
E2

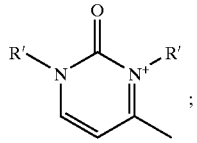
E3

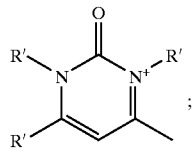
E4

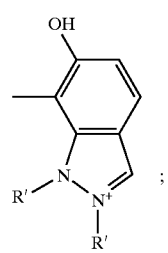
E5

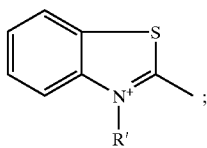
E6

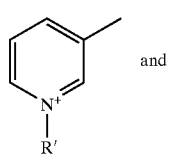
E7 and

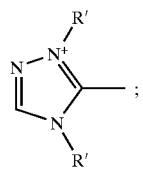
E8 in which R' represents a $C_1$–$C_4$ alkyl radical; when m=0 and when $D_1$ represents a nitrogen atom, then E can also denote a group of structure E9 below:

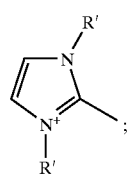
E9 in which R' represents a $C_1$–$C_4$ alkyl radical, and at least one nitrobenzene direct dye.

The ready-to-use dye composition in accordance with the invention leads to intense, chromatic colorations which show low selectivity and excellent properties of resistance both with respect to atmospheric agents such as light and bad weather and with respect to perspiration and the various treatments to which the hair may be subjected (washing, permanent-waving).

A subject of the invention is also a process for dyeing keratin fibres using this ready-to-use dye composition.

The cationic direct dyes of formulae (I), (II), (III) and (III') which can be used in the ready-to-use dye compositions in accordance with the invention are known compounds and are described, for example, in patent applications WO 95/01772, WO 95/15144 and EP-A-0,714,954.

Among the cationic direct dyes of formula (I) which can be used in the ready-to-use dye compositions in accordance with the invention, mention may be made more particularly of the compounds corresponding to structures (I1) to (I52) below:

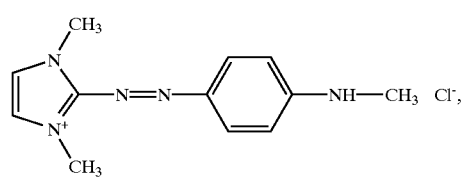
(I1)

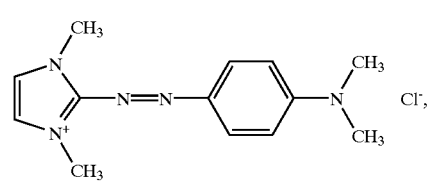
(I2)

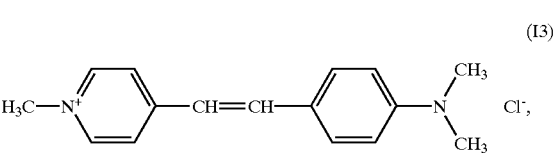
(I3)

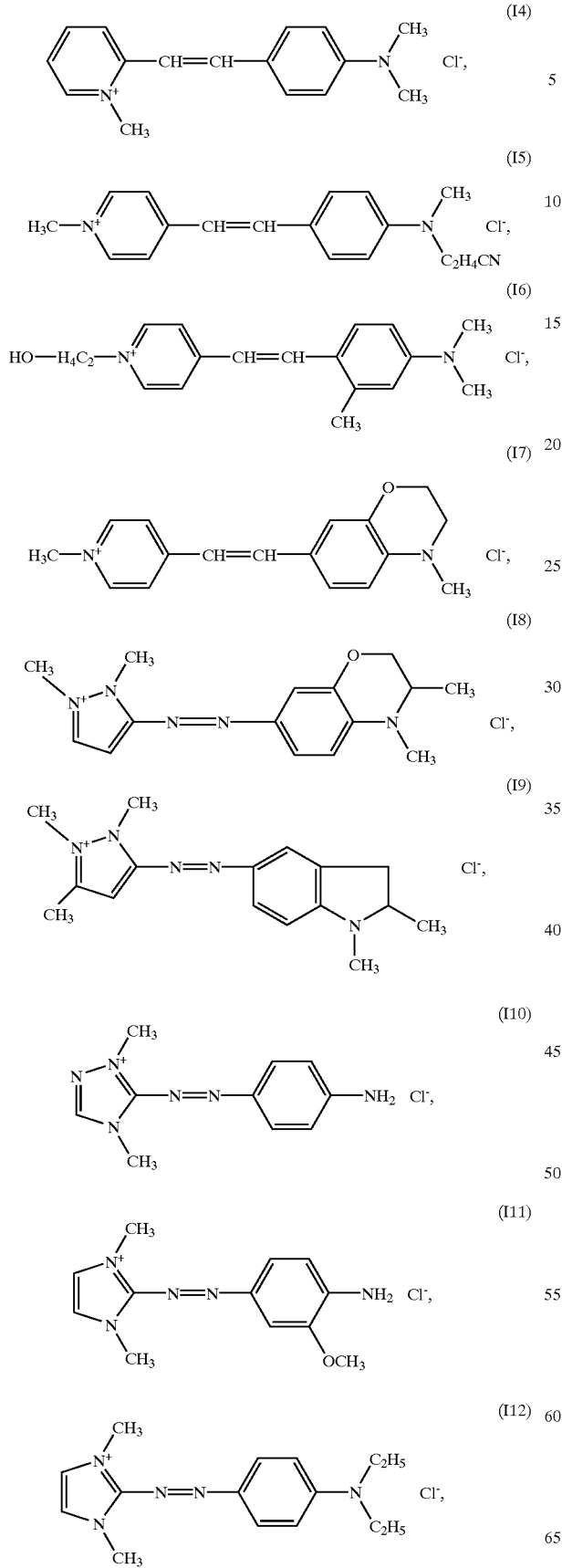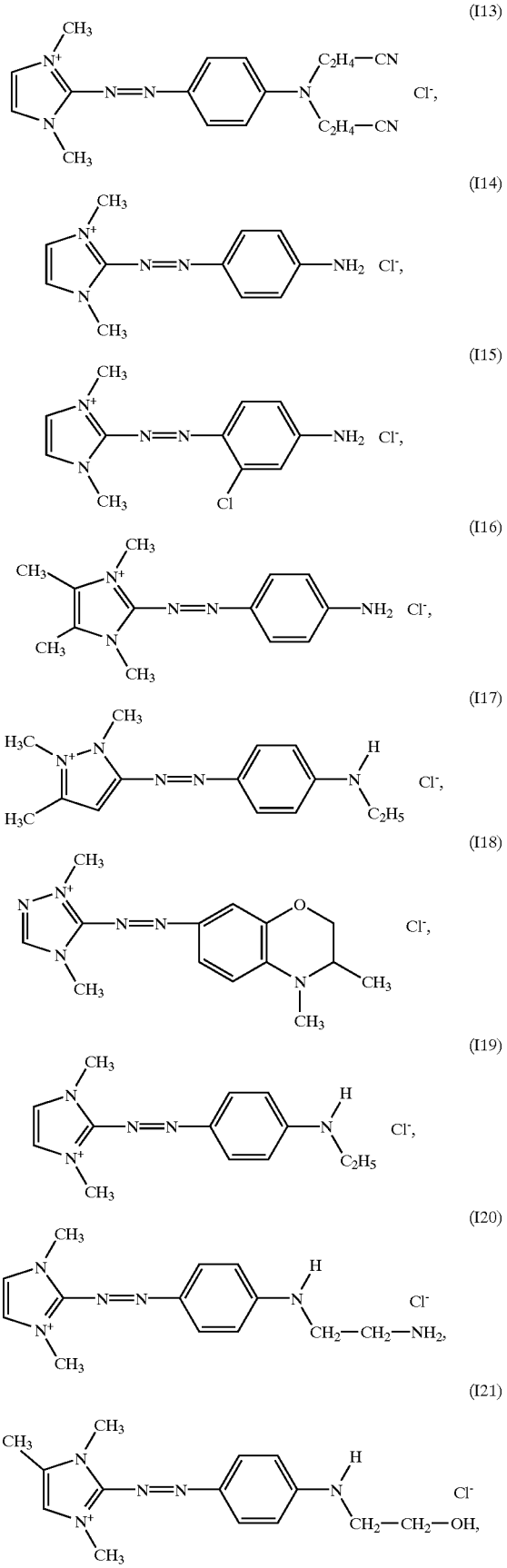

(I22) 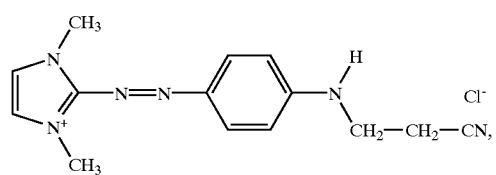
(I23) 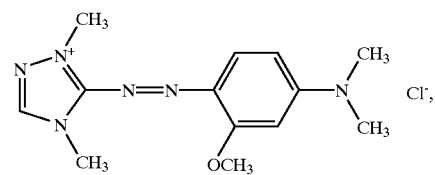
(I24) 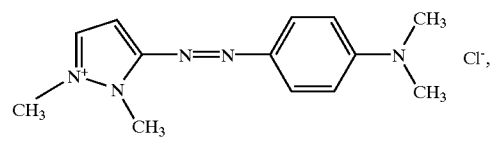
(I25) 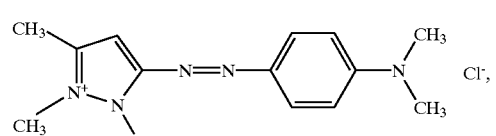
(I26) 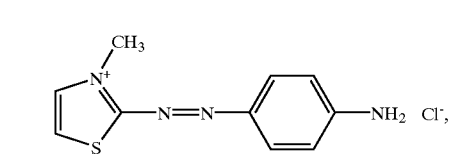
(I27) 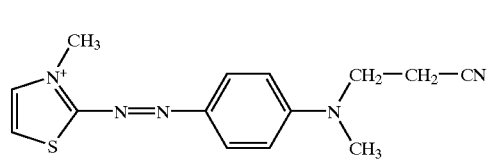
(I28) 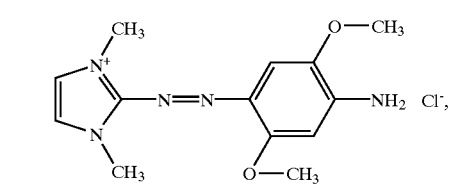
(I29) 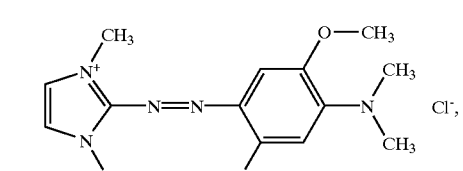
(I30) 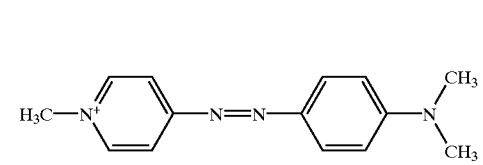
(I31) 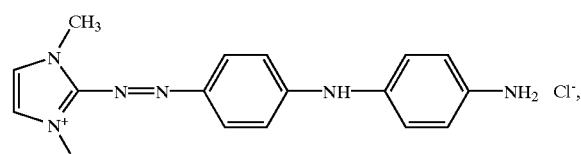
(I32) 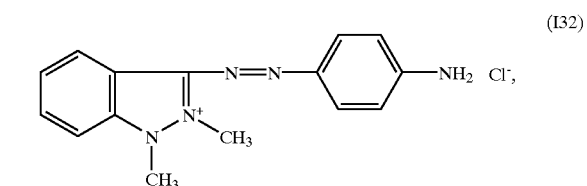
(I33) 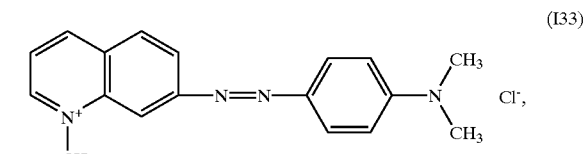
(I34) 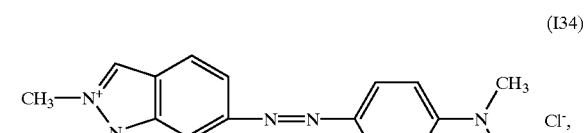
(I35) 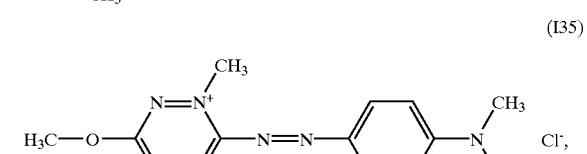
(I36) 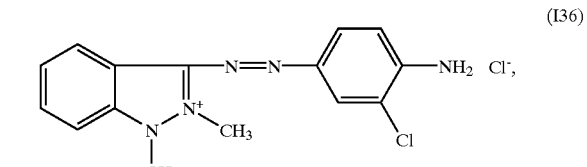
(I37) 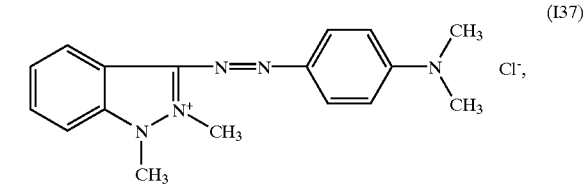
(I38) 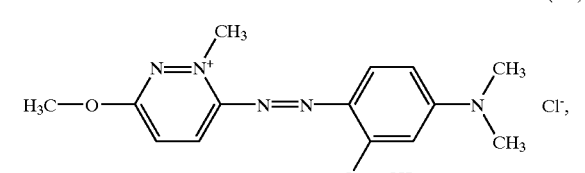
(I39) 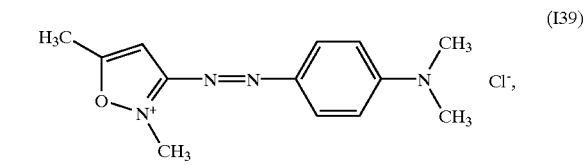

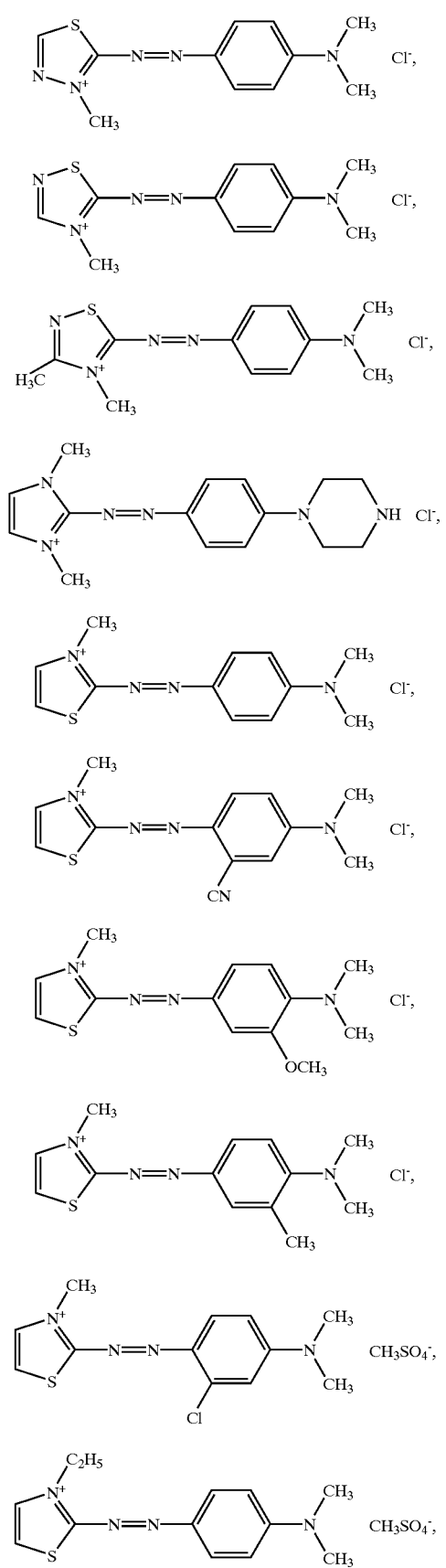
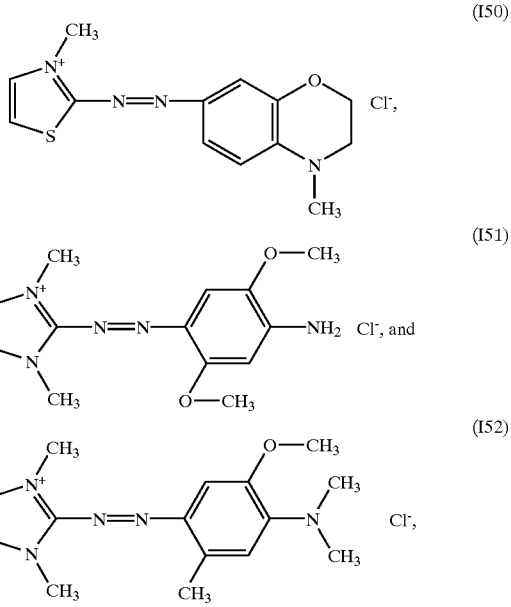

Among the compounds of structures (I1) to (I52) described above, the compounds most particularly preferred are those corresponding to structures (I1), (I2), (I14) and (I31).

Among the cationic direct dyes of formula (II) which can be used in the ready-to-use dye compositions in accordance with the invention, mention may be made more particularly of the compounds corresponding to structures (II1) to (II12) below:

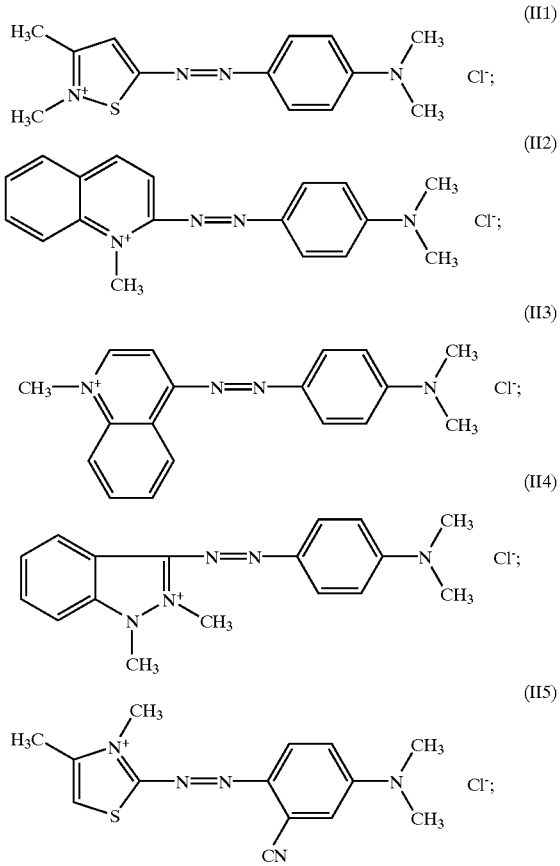

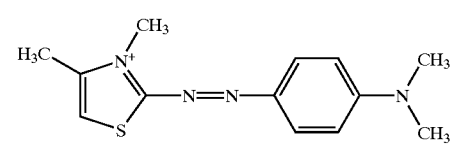 (II6) CH₃SO₄⁻;

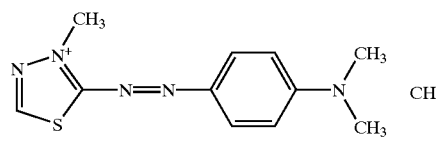 (II7) CH₃SO₄⁻;

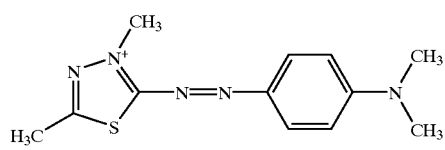 (II8) CH₃SO₄⁻;

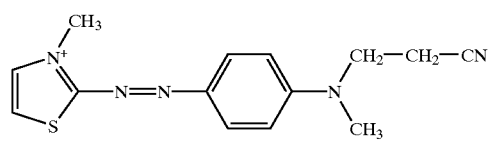 (II9) Cl⁻;

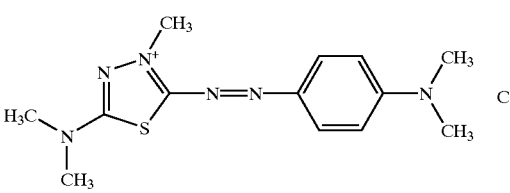 (II10) CH₃SO₄⁻;

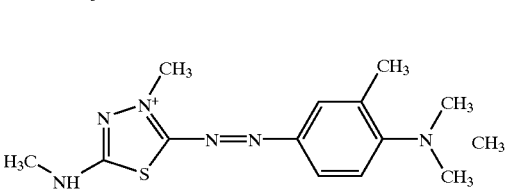 (II11) CH₃SO₄⁻; and

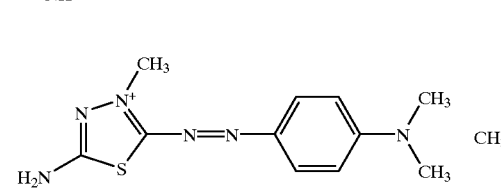 (II12) CH₃SO₄⁻.

Among the cationic direct dyes of formula (III) which can be used in the ready-to-use dye compositions in accordance with the invention, mention may be made more particularly of the compounds corresponding to structures (III1) to (III18) below:

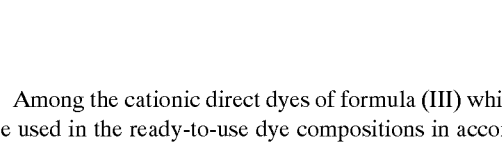 (III1) Cl⁻;

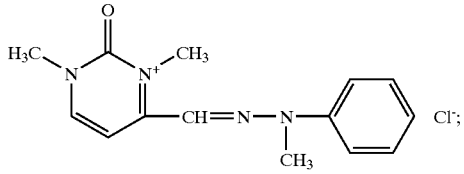 (III2) Cl⁻;

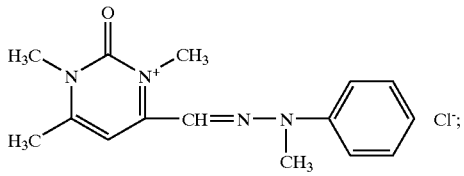 (III3) Cl⁻;

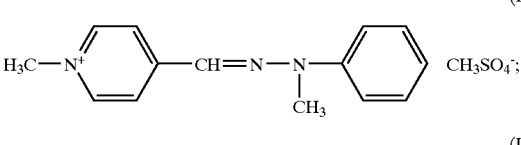 (III4) CH₃SO₄⁻;

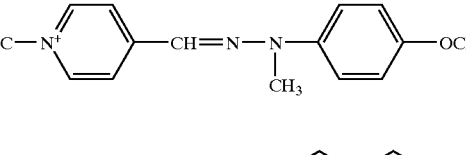 (III5) Cl⁻;

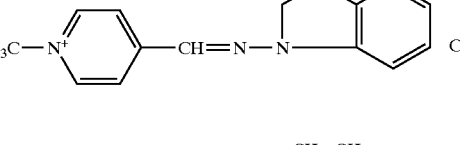 (III6) CH₃SO₄⁻;

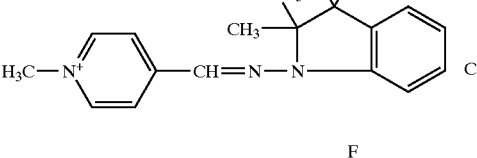 (III7) CH₃SO₄⁻;

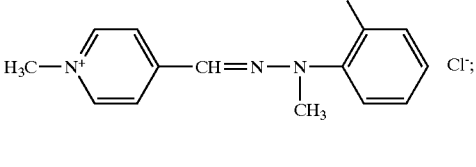 (III8) Cl⁻;

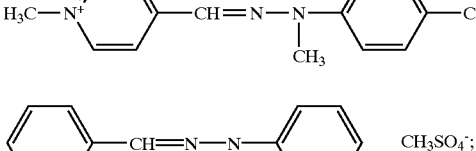 (III9) Cl⁻;

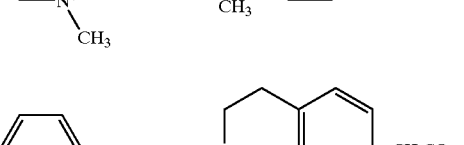 (III10) CH₃SO₄⁻;

 (III11) CH₃SO₄⁻;

(III12)

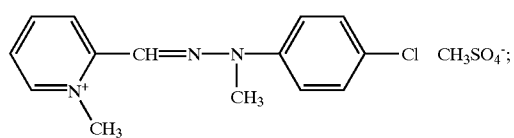

(III13)

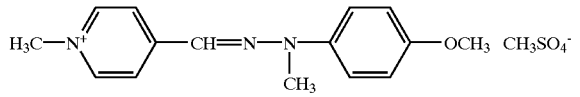

(III14)

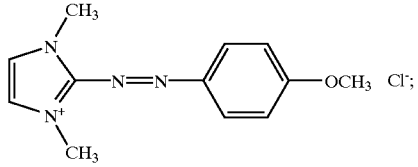

(III15)

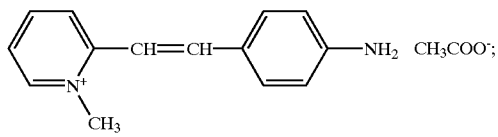

(III16)

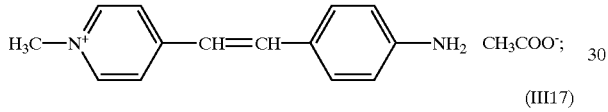

(III17)

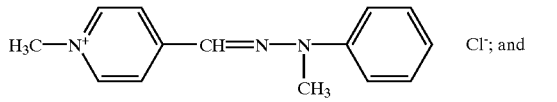

(III18)

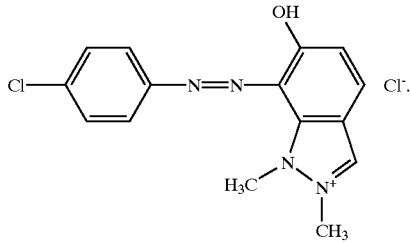

Among the specific compounds of structures (III1) to (III18) described above, the compounds most particularly preferred are those corresponding to structures (III4), (III5) and (III13).

Among the cationic direct dyes of formula (III') which can be used in the ready-to-use dye compositions in accordance with the invention, mention may be made more particularly of the compounds corresponding to structures (III'1) to (III'3) below:

(III'1)

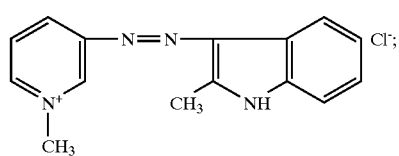

(III'2)

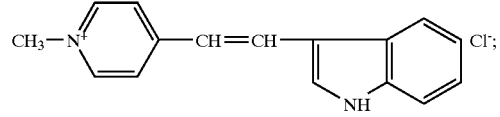

and (III'3)

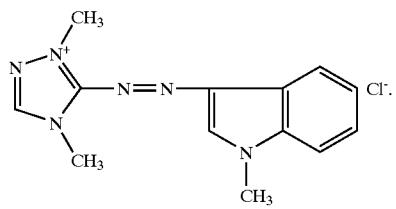

The cationic direct dye(s) used according to the invention preferably represent(s) from 0.001 to 10% by weight approximately relative to the total weight of the ready-to-use dye composition, and even more preferably from 0.05 to 5% by weight approximately relative to this weight.

The nitrobenzene direct dye(s) which can be used in the ready-to-use dye composition in accordance with the invention is (are) preferably chosen from the compounds of formula (IV) below:

(IV)

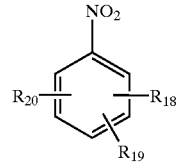

in which:

$R_{18}$ represents an amino radical; an amino radical monosubstituted or disubstituted with a $C_1$–$C_4$ alkyl, $C_1$–$C_4$ monohydroxyalkyl, $C_2$–$C_4$ polyhydroxyalkyl, $C_1$–$C_4$ aminoalkyl, mono($C_1$–$C_4$) alkylamino($C_1$–$C_4$) alkyl, di($C_1$–$C_4$)alkylamino($C_1$–$C_4$)alkyl or ureido($C_1$–$C_4$)alkyl or aryl radical or an aryl radical in which the aryl ring is substituted with one or more hydroxyl, carboxyl, amino or di($C_1$–$C_4$)alkylamino radicals, $R_{19}$ represents a hydrogen atom; an amino radical; hydroxyl radical; $C_1$–$C_4$ alkyl radical; $C_1$–$C_4$ alkoxy radical; $C_1$–$C_4$ monohydroxyalkyl radical; $C_2$–$C_4$ polyhydroxyalkyl radical; $C_1$–$C_4$ monohydroxyalkoxy radical; $C_2$–$C_4$ polyhydroxyalkoxy radical; $C_1$–$C_4$ aminoalkoxy radical; an amino radical monosubstituted or disubstituted with a $C_1$–$C_4$ alkyl, $C_1$–$C_4$ monchydroxyalkyl, $C_2$–$C_4$ polyhydroxyalkyl, $C_1$–$C_4$ aminoalkyl, mono ($C_1$–$C_4$) alkylamino($C_1$–$C_4$)alkyl, di($C_1$–$C_4$)alkylamino($C_1$–$C_4$)alkyl or ureido($C_1$–$C_4$)alkyl or aryl radical or an aryl radical in which the aryl ring is substituted with one or more hydroxyl, carboxyl, amino or di($C_1$–$C_4$)alkylamino radicals;

$R_{20}$ represents a hydrogen or halogen atom, a $C_1$–$C_4$ alkyl radical or a nitro group.

Among the nitrobenzene dyes of formula (IV) above, mention may be made most particularly of:

2-amino-4-methyl-5-N-(β-hydroxyethyl)aminonitrobenzene,

4-N-(β-ureidoethyl)aminonitrobenzene, 4-(N-ethyl-N-β-hydroxyethyl)amino-1-N-(β-hydroxyethyl)aminonitrobenzene, 2-N-(β-hydroxyethyl)amino-5-methylnitrobenzene, 5-chloro-3-N-(ethyl)amino-4-hydroxynitrobenzene,
5-amino-3-chloro-4-hydroxynitrobenzene,
2-N-(γ-hydroxypropyl)amino-5-N,N-bis(β-hydroxyethyl)-aminonitrobenzene,
5-hydroxy-2-N-(γ-hydroxypropyl)aminonitrobenzene,
1,3-bis(β-hydroxyethyl)amino-4-chloro-6-nitrobenzene,
2,4-diaminonitrobenzene,
3,4-diaminonitrobenzene,
2,5-diaminonitrobenzene,
3-amino-4-hydroxynitrobenzene,
4-amino-3-hydroxynitrobenzene,
5-amino-2-hydroxynitrobenzene,
2-amino-5-hydroxynitrobenzene,
4-amino-3-hydroxynitrobenzene,
5-amino-2-hydroxynitrobenzene,
2-amino-3-hydroxynitrobenzene,
2-amino-5-N-(β-hydroxyethyl)aminonitrobenzene,
2-amino-5-N,N-bis(β-hydroxyethyl)aminonitrobenzene,
2,5-N,N'-(β-hydroxyethyl)aminonitrobenzene,
2-N-(β-hydroxyethyl)amino-5-N,N-bis(β-hydroxyethyl)-aminonitrobenzene,
2-amino-5-N-(methyl)aminonitrobenzene,
2-N-(methyl)amino-5-N,N-bis(β-hydroxyethyl)aminonitrobenzene,
2-N-(methyl)amino-5-(N-methyl-N-β-hydroxyethyl)aminonitrobenzene,
2,5-N,N'-(β-hydroxyethyl)aminonitrobenzene,
2-N-(β-hydroxyethyl)amino-5-hydroxynitrobenzene,
3-methoxy-4-N-(β-hydroxyethyl)aminonitrobenzene,
2-N-(methyl)amino-4-β-hydroxyethyloxynitrobenzene,
2-amino-3-methylnitrobenzene,
2-N-(β-hydroxyethyl)amino-5-aminonitrobenzene,
2-amino-4-chloro-5-N-(β-hydroxyethyl)aminonitrobenzene,
2-amino-4-methyl-5-N-(β-hydroxyethyl)aminonitrobenzene,
2-amino-4-methyl-5-N-(methyl)aminonitrobenzene,
2-N-(β-hydroxyethyl)amino-5-methoxynitrobenzene,
2-amino-5-β-hydroxyethyloxynitrobenzene,
2-N-(β-hydroxyethyl)aminonitrobenzene,
3-amino-4-N-(β-hydroxyethyl)aminonitrobenzene,
3-β-hydroxyethyloxy-4-N-(β-hydroxyethyl)aminonitrobenzene,
2-N-(methyl)amino-4-β,γ-dihydroxypropyloxynitrobenzene,
2-N-(β-hydroxyethyl)amino-5-β-hydroxyethyloxynitrobenzene,
2-N-(β-hydroxyethyl)amino-5-β,γ-dihydroxypropyloxynitrobenzene,
2-hydroxy-4-N-(β-hydroxyethyl)aminonitrobenzene,
2-N-(methyl)amino-4-methyl-5-aminonitrobenzene,
2-amino-4-isopropyl-5-N-(methyl)aminonitrobenzene,
2-N-(methyl)amino-5-(N-methyl-N-β,γ-dihydroxypropyl)aminonitrobenzene,
3-N-(β-hydroxyethyl)amino-4-N-(β-hydroxyethyl)aminonitrobenzene,
2-amino-4-methyl-5-N-(β,γ-dihydroxypropyl)aminonitrobenzene,
2-amino-4-methyl-5-hydroxynitrobenzene,
2-N-(β-hydroxyethyl)amino-4-N-(β-hydroxyethyl)aminonitrobenzene,
2-amino-5-N-(β-aminoethyl)aminonitrobenzene,
2-N-(β-aminoethyl)amino-5-methoxynitrobenzene,
2-N-(methyl)amino-5-N-(β-aminoethyl)aminonitrobenzene,
2-N-(β-aminoethyl)amino-4-N,N-(dimethyl)aminonitrobenzene,
3-amino-4-N-(β-aminoethyl)aminonitrobenzene,
2-amino-4-methyl-5-N-(β-aminoethyl)aminonitrobenzene,
2-N-(β-aminoethyl)amino-5-N,N-bis(β-hydroxyethyl)aminonitrobenzene,
3-β-aminoethyloxy-4-aminonitrobenzene,
2-N-(methyl)amino-5-(N-δ-amino-n-butyl)aminonitrobenzene,
2-N-(γ-amino-n-propyl)amino-5-N,N-(dimethyl)aminonitrobenzene,
3-methoxy-4-N-(β-aminoethyl)aminonitrobenzene,
2-N-(β-aminoethyl)amino-5-aminonitrobenzene,
2-amino-4-chloro-5-N-(β-aminoethyl)aminonitrobenzene,
2-N-(β-aminoethyl)amino-4-methoxynitrobenzene,
2-N-(β-aminoethyl)aminonitrobenzene,
2-N-(β-aminoethyl)amino-5-N-(β-aminoethyl)aminonitrobenzene,
2-N-(β-aminoethyl)amino-4-β-hydroxyethyloxynitrobenzene,
3-β-hydroxyethyloxy-4-N-(β-aminoethyl)aminonitrobenzene,
2-amino-5-aminoethyloxynitrobenzene,
3-hydroxy-4-N-(β-aminoethyl)aminonitrobenzene,
2-N-(β-aminoethyl)amino-5-β-hydroxyethyloxynitrobenzene,
2-N-(β-aminoethyl)amino-4-hydroxynitrobenzene,
2-{[2-hydroxy-3-N-(β-hydroxyethyl)amino-6-nitro]benzyloxy}ethylamine, and
2-{[2-hydroxy-3-N-(β-hydroxypropyl)amino-6-nitro]benzyloxy}ethylamine.

Among the nitrobenzene dyes of formula (IV) above, the ones most particularly preferred are:
2-amino-4-methyl-5-N-(β-hydroxyethyl)aminonitrobenzene,
4-N-(β-ureidoethyl)aminonitrobenzene,
4-(N-ethyl-N-β-hydroxyethyl)amino-1-N-(β-hydroxyethyl)aminonitrobenzene,
2-N-(β-hydroxyethyl)amino-5-methylnitrobenzene,
5-chloro-3-N-(ethyl)amino-4-hydroxynitrobenzene,
5-amino-3-chloro-4-hydroxynitrobenzene,
2-N-(γ-hydroxypropyl)amino-5-N,N-bis(β-hydroxyethyl)-aminonitrobenzene,
5-hydroxy-2-N-(γ-hydroxypropyl)aminonitrobenzene,
1,3-bis(β-hydroxyethyl)amino-4-chloro-6-nitrobenzene,
3,4-diaminonitrobenzene,
2-amino-5-hydroxynitrobenzene,
2-amino-3-hydroxynitrobenzene,
2-amino-5-N-(β-hydroxyethyl)aminonitrobenzene,
2-amino-5-N,N-bis(β-hydroxyethyl)aminonitrobenzene,
2-N-(β-hydroxyethyl)amino-5-N,N-bis(β-hydroxyethyl)-aminonitrobenzene,
2-N-(β-hydroxyethyl)amino-5-hydroxynitrobenzene,
2-N-(β-hydroxyethyl)amino-5-aminonitrobenzene,
2-N-(β-aminoethyl) amino-4-methoxynitrobenzene, and
2-N-(β-aminoethyl)amino-5-β-hydroxyethyloxynitrobenzene The nitrobenzene dye(s) preferably represent(s) from 0.0005 to 15% by weight approximately relative to the total weight of the ready-to-use dye composition in accordance with the invention, and even more preferably from 0.005 to 10% by weight approximately relative to this weight.

The ready-to-use dye composition in accordance with the invention can also contain one or more oxidation bases and/or one or more couplers. These oxidation bases can be chosen in particular from para-phenylenediamines, para-aminophenols, ortho-phenylenediamines and heterocyclic bases such as, for example, pyridine derivatives, pyrimidine derivatives, pyrazole derivatives and pyrazolopyrimidine derivatives. The couplers can be chosen in particular from meta-phenylenediamines, meta-aminophenols, meta-diphenols, heterocyclic couplers such as, for example, indole derivatives, indoline derivatives, benzimidazole derivatives, benzomorpholine derivatives, sesamol derivatives, pyridine, pyrimidine and pyrazole derivatives, and the addition salts thereof with an acid.

When they are present, the oxidation base(s) preferably represent(s) from 0.0005 to 12% by weight approximately relative to the total weight of the dye composition in accordance with the invention, and even more preferably from 0.005 to 8% by weight approximately relative to this weight.

When they are present, the coupler(s) preferably represent(s) from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

When one or more oxidation bases and/or one or more couplers are used, the ready-to-use dye composition can then also contain at least one oxidizing agent chosen, for example, from hydrogen peroxide, urea peroxide, alkali metal bromates, persalts such as perborates and persulphates, and enzymes such as peroxidases and two-electron oxidoreductases.

Among the 2-electron oxidoreductases which can be used as oxidizing agents in the ready-to-use dye composition in accordance with the invention, mention may be made more particularly of pyranose oxidases, glucose oxidases, glycerol oxidases, lactate oxidases, pyruvate oxidases and uricases.

According to the invention, the use of uricases of animal, microbiological or biotechnological origin is particularly preferred.

By way of example, mention may be made in particular of the uricase extracted from boar liver, the uricase from *Arthrobacter globiformis* and the uricase from *Aspergillus flavus*.

The 2-electron oxidoreductase(s) can be used in pure crystalline form or in a form diluted in a diluent which is inert with respect to the said 2-electron oxidoreductase.

When they are used, the 2-electron oxidoreductase(s) preferably represent(s) from 0.01 to 20% by weight approximately relative to the total weight of the ready-to-use dye composition, and even more preferably from 0.1 to 5% by weight approximately relative to this weight.

When an enzyme of 2-electron oxidoreductase type is used in accordance with the invention, the ready-to-use dye composition can also contain one or more donors for the said enzyme.

According to the invention, the term "donor" refers to the various substrates involved in the functioning of the said 2-electron oxidoreductase(s).

The nature of the donor (or substrate) used varies as a function of the nature of the 2-electron oxidoreductase which is used. For example, D-glucose, L-sorbose and D-xylose may be mentioned as donors for pyranose oxidases; D-glucose may be mentioned as a donor for glucose oxidases; glycerol and dihydroxyacetone may be mentioned as donors for glycerol oxidases; lactic acid and its salts may be mentioned as donors for lactate oxidases; pyruvic acid and its salts may be mentioned as donors for pyruvate oxidases; and lastly, uric acid and its salts may be mentioned as donors for uricases.

When they are used, the donor(s) (or substrate(s)) preferably represent(s) from 0.01 to 20% by weight approximately relative to the total weight of the ready-to-use dye composition in accordance with the invention, and even more preferably from 0.1 to 5% approximately relative to this weight.

The medium which is suitable for dyeing (or support) for the ready-to-use dye composition in accordance with the invention generally consists of water or of a mixture of water and at least one organic solvent to dissolve the compounds which would not be sufficiently water-soluble. As organic solvents, mention may be made, for example, of $C_1$–$C_4$ alkanols, such as ethanol and isopropanol, as well as aromatic alcohols such as benzyl alcohol or phenoxyethanol, similar products and mixtures thereof.

The pH of the ready-to-use dye composition in accordance with the invention is generally between 5 and 11 approximately and preferably between 6.5 and 10 approximately. It can be adjusted to the desired value by means of acidifying or basifying agents usually used for dyeing keratin fibres.

Among the acidifying agents, mentioned may be made, by way of example, of inorganic or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, by way of example, of aqueous ammonia, alkaline carbonates, alkanolamines such as mono-, di- and triethanolamine, 2-methyl-2-amino-1-propanol and derivatives thereof, sodium hydroxide, potassium hydroxide and the compounds of formula (V) below:

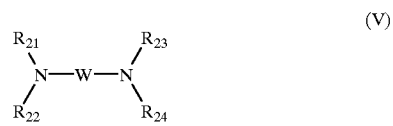

in which W is a propylene residue optionally substituted with a hydroxyl group or a $C_1$–$C_4$ alkyl radical; $R_{21}$, $R_{22}$, $R_{23}$ and $R_{24}$, which may be identical or different, represent a hydrogen atom or a $C_1$–$C_4$ alkyl or $C_1$–$C_4$ hydroxyalkyl radical.

The ready-to-use dye composition in accordance with the invention can also contain various adjuvants conventionally used in compositions for dyeing the hair, such as, for example, antioxidants, penetrating agents, sequestering agents, fragrances, buffers, dispersing agents, film-forming agents, preserving agents and opacifiers.

Needless to say, a person skilled in the art will take care to select this or these optional complementary compounds such that the advantageous properties intrinsically associated with the ready-to-use dye composition in accordance with the invention are not, or are not substantially, adversely affected by the addition(s) envisaged.

The ready-to-use dye composition in accordance with the invention can be in various forms, such as in the form of liquids, creams or gels, which may be pressurized, or in any other form which is suitable for dyeing keratin fibres, and in particular human hair.

When the ready-to-use dye composition in accordance with the invention contains at least one oxidation base and/or at least one coupler and at least one oxidizing agent, it must then be free of gaseous oxygen, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more precisely between 5 and 40 minutes.

According to one specific embodiment of the invention, and when the dye composition in accordance with the invention contains at least one oxidation base and/or at least one coupler, the process includes a preliminary step which consists in separately storing, on the one hand, a composition (A) comprising, in a medium which is suitable for dyeing, at least one cationic direct dye as defined above, at least one nitrobenzene direct dye and at least one oxidation base and/or at least one coupler, and, on the other hand, a composition (B) containing, in a medium which is suitable for dyeing, at least one oxidizing agent, and then in mixing them together at the time of use, before applying this mixture to the keratin fibres.

Another subject of the invention is a multi-compartment dyeing device or "kit" or any other multi-compartment packaging system, a first compartment of which contains composition (A) as defined above and a second compartment of which contains composition (B) as defined above. These devices can be equipped with a means for applying the desired mixture to the hair, such as the devices described in patent FR-2,586,913 in the name of the Applicant.

The examples which follow are intended to illustrate the invention without, however, limiting its scope.

EXAMPLES

Dyeing Examples 1 and 2

The following ready-to-use dye compositions were prepared (contents in grams):

| COMPOSITION | 1 | 2 |
|---|---|---|
| 2-Amino-5-hydroxynitrobenzene (nitrobenzene direct dye) | 0.35 | — |
| 2-N- (β-Hydroxyethyl) amino-5-amino-nitrobenzene (nitrobenzene direct dye) | — | 0.25 |
| Orange-coloured cationic direct dye of structure (I4) | 0.065 | — |
| Red cationic direct dye of structure (I1) | — | 0.04 |
| Common dye support (*) | (*) | (*) |
| Demineralized water q.s. | 100 g | 100 g |

| (*): Common dye support: | |
|---|---|
| Ethanol | 20.0 g |
| Nonylphenol oxyethylenated with 9 mol of ethylene oxide, sold under the name Igepal NR 9 OR by the company Rhodia Chemie | 8.0 g |
| 2-Amino-2-methyl-1-propanol q.s. | pH = 7.5 |

Each of the ready-to-use dye compositions described above was applied to locks of natural grey hair containing 90% white hairs for 30 minutes. The hair was then rinsed, washed with a standard shampoo and then dried.

The hair was dyed in the shades featured in

| EXAMPLE | Shade obtained |
|---|---|
| 1 | Coppery |
| 2 | Red mahogany |

What is claimed is:

1. A ready-to-use composition for dyeing keratin fibers, comprising:

at least one nitrobenzene direct dye; and, at least one cationic direct dye chosen from:
(a) compounds of formula (I), below:

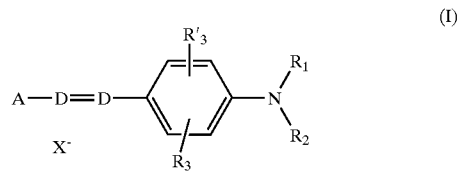

wherein:

X is an anion;

$R_1$ and $R_2$, which may be identical or different, are chosen from a hydrogen atom, a 4'-aminophenyl radical, and $C_1$–$C_4$ alkyl radicals which can be substituted with a —CN, —OH or —NH$_2$ radical, or form, with a carbon atom of the benzene ring, an optionally oxygenated or nitrogenous heterocycle which can be substituted with one or more $C_1$–$C_4$ alkyl radicals;

$R_3$ and $R'_3$, which may be identical or different, are chosen from a hydrogen atom halogen atoms chosen from chlorine, bromine, iodine and fluorine, cyano radicals, $C_1$–$C_4$ alkoxy radicals, and acetyloxy radicals;

D is chosen from a nitrogen atom and a —CH group;

A is chosen from structures A1 to A19, below:

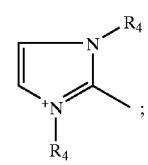

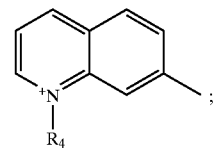

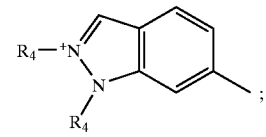

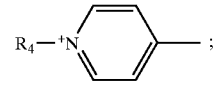

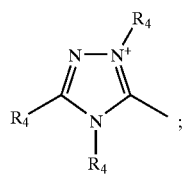
A₅

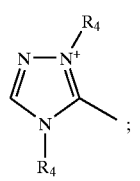
A₆

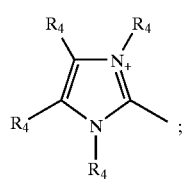
A₇

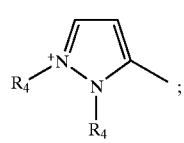
A₈

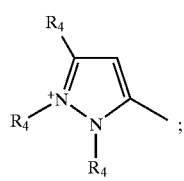
A₉

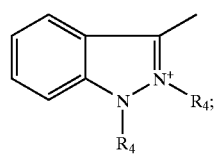
A₁₀

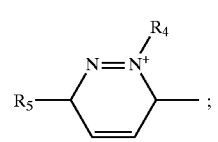
A₁₁

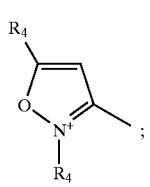
A₁₂

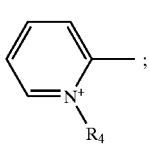
A₁₃

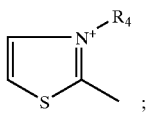
A₁₄

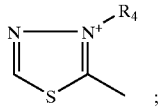
A₁₅

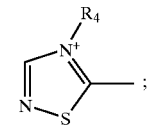
A₁₆

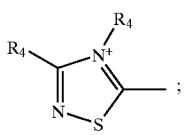
A₁₇

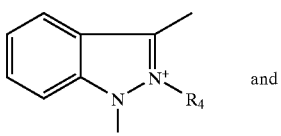
and A₁₈

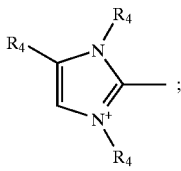
A₁₉ wherein $R_4$ is chosen from $C_1$–$C_4$ alkyl radicals which can be substituted with a hydroxyl radical and $R_5$ is chosen from $C_1$–$C_4$ alkoxy radicals, and further wherein when D is a —CH group, when A is $A_4$ or $A_{13}$, and when $R_3$ is other than an alkoxy radical, then $R_1$ and $R_2$ are not simultaneously a hydrogen atom, and further wherein when D is a nitrogen atom, A is chosen from $A_1$–$A_{12}$ and $A_{14}$–$A_{19}$;

(b) compounds of formula (II), below:

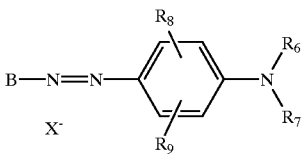

(II)

wherein:

$R_6$ is chosen from a hydrogen atom and $C_1$–$C_4$ alkyl radicals;

$R_7$ is chosen from a hydrogen atom, alkyl radicals which can be substituted with a —CN radical or with an amino group, and a 4'-aminophenyl radical, or forms, with $R_6$, a heterocycle, which can be oxygenated or nitrogenous, and which can be substituted with at least one $C_1$–$C_4$ alkyl radical;

$R_8$ and $R_9$, which may be identical or different, are chosen from a hydrogen atom, halogen atoms, $C_1$–$C_4$ alkyl radicals, $C_1$–$C_4$ alkoxy radicals, and a —CN radical;

$X^-$ is an anion;

B is chosen from structures B1 to B6, below:

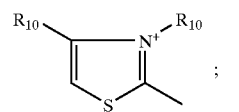
B1

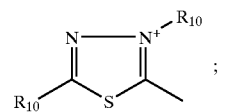
B2

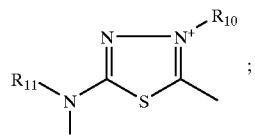
B3

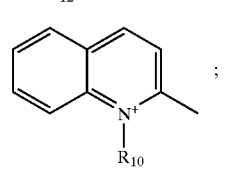
B4

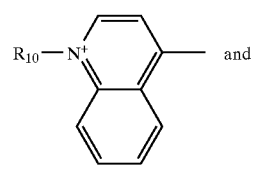
B5

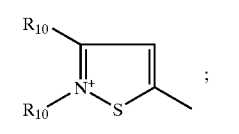
B6 wherein:
$R_{10}$ is chosen from $C_1$–$C_4$ alkyl radicals;
$R_{11}$ and $R_{12}$, which may be identical or different, are chosen from a hydrogen atom and $C_1$–$C_4$ alkyl radicals;
(c) compounds of formula (III) and compounds of formula (III') below:

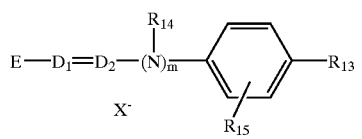
(III)

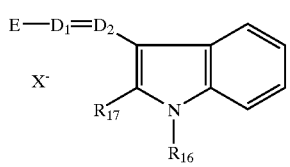
(III')

wherein
$R_{13}$ is chosen from a hydrogen atom, $C_1$–$C_4$ alkoxy radicals, halogen atoms, and amino radicals;
$R_{14}$ is chosen from a hydrogen atom and $C_1$–$C_4$ alkyl radicals, or forms, with a carbon atom of the benzene ring, a heterocycle which is optionally oxygenated and which can be substituted with at least one $C_1$–$C_4$ alkyl group, $R_{15}$ is chosen from a hydrogen atom and halogen atoms;
$R_{16}$ and $R_{17}$, which may be identical or different, are chosen from a hydrogen atom and $C_1$–$C_4$ alkyl radicals;
$D_1$ and $D_2$, which may be identical or different, are chosen from a nitrogen atom and a —CH group;
$X^-$ is an anion;
m=0 or 1,
wherein when $R_{13}$ is an unsubstituted amino group, then $D_1$ and $D_2$ simultaneously are a —CH group and m=0; and
E is chosen from structures E1 to E8 below:

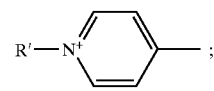
E1

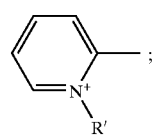
E2

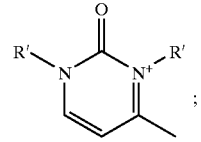
E3

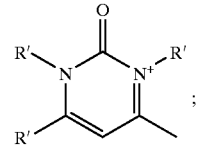
E4

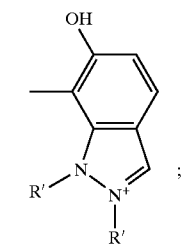
E5

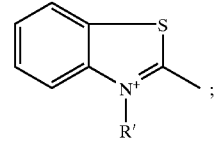
E6

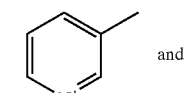
E7

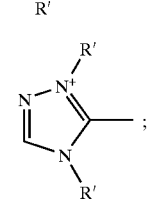
E8 and with the proviso that when m=0 and $D_1$ is a nitrogen atom, then E can also be chosen from E9 below:

E9

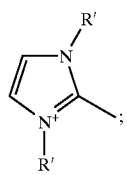

wherein R' for structures E1 to E9 is chosen from $C_1$–$C_4$ alkyl radicals, and with the further proviso that in said compounds of formula (III) when $D_1$ and $D_2$ are simultaneously nitrogen atoms, m=0, $R_{13}$ is an amino radical and $R_{15}$ is a hydrogen atom, then E is chosen from $E_1$, $E_3$ to $E_5$, $E_7$ and $E_8$.

2. The composition according to claim 1 wherein $X^-$ is chosen from chloride, methyl sulfate and acetate.

3. The composition according to claim 1 wherein at least one of $R_8$, $R_9$, $R_{13}$, and $R_{15}$ is a halogen atom chosen from chlorine, bromine, iodine and fluorine.

4. The composition according to claim 1, wherein said at least one cationic direct dye of formula (I) is chosen from compounds of structures (I1) to (I52) below:

(I1)
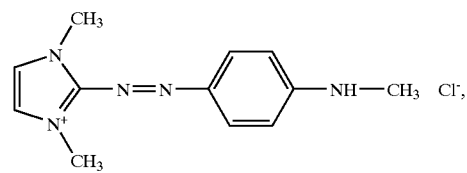

(I2)
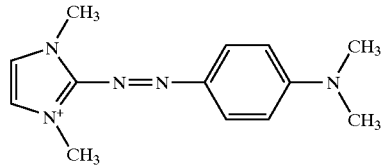

(I3)
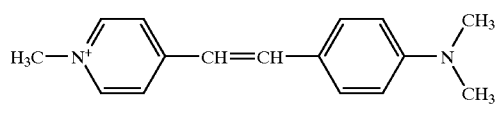

(I4)
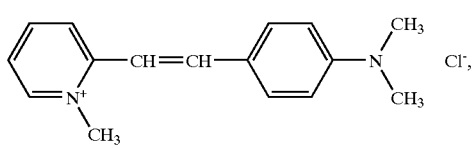

(I5)
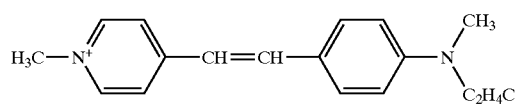

(I6)
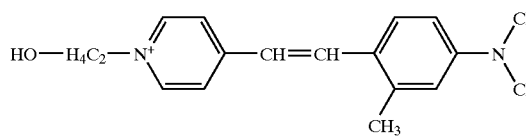

(I7)
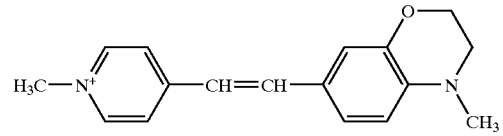

(I8)
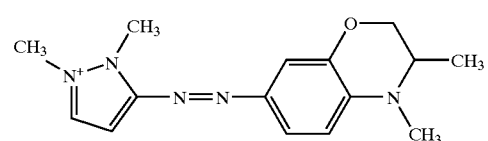

(I9)
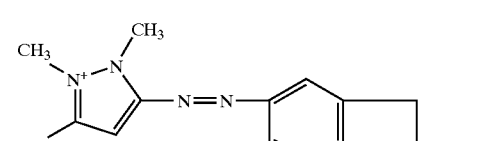

(I10)
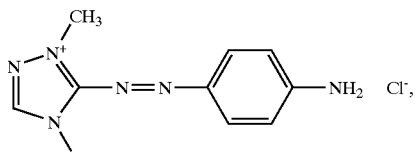

(I11)
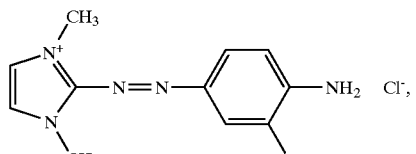

(I12)
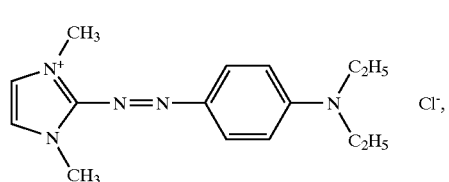

(I13)
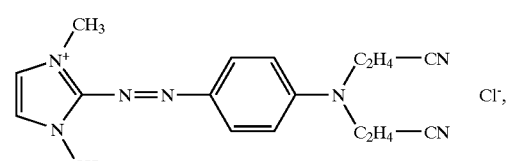

(I14)
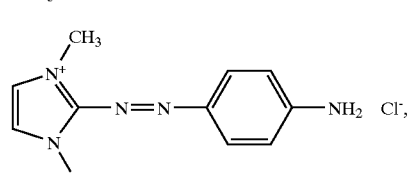

(I15)
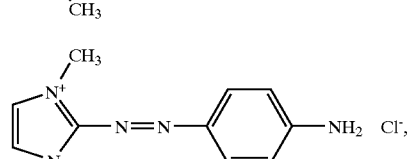

-continued
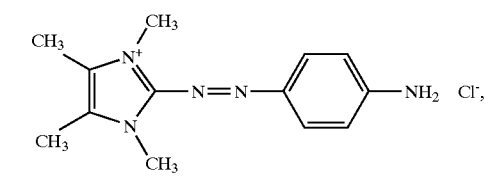 (I16)
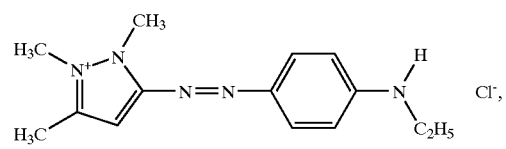 (I17)
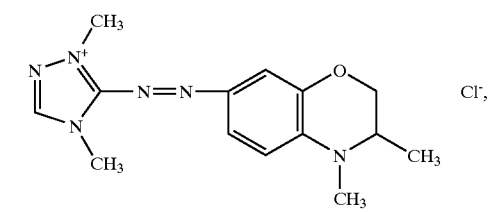 (I18)
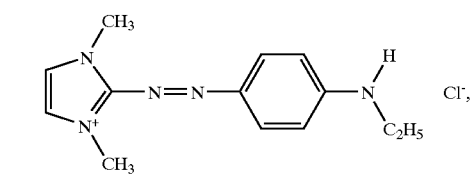 (I19)
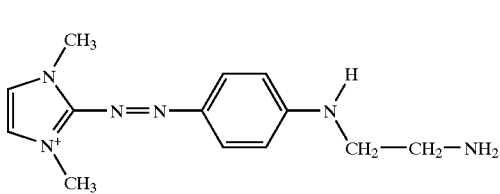 (I20)
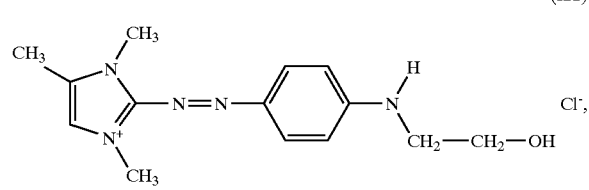 (I21)
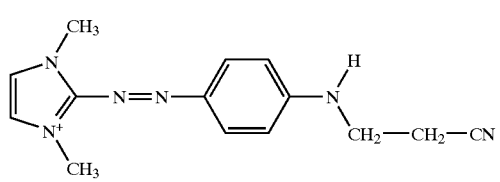 (I22)
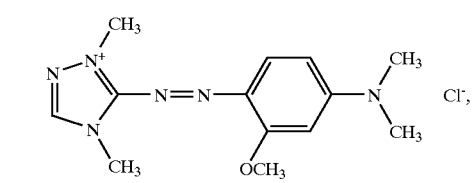 (I23)
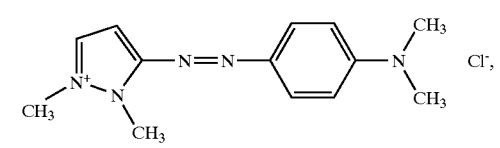 (I24)
-continued
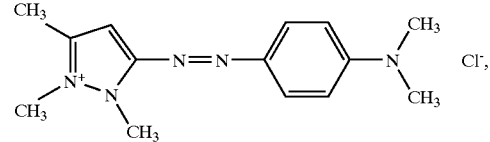 (I25)
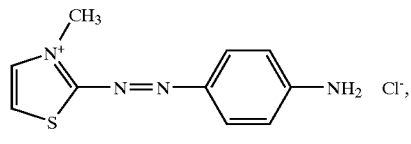 (I26)
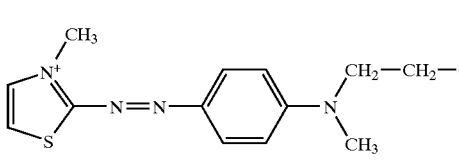 (I27)
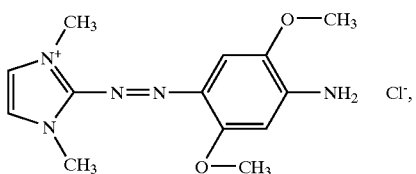 (I28)
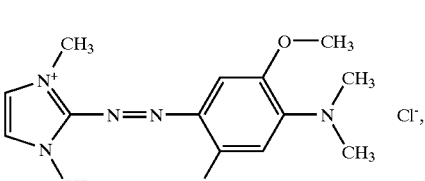 (I29)
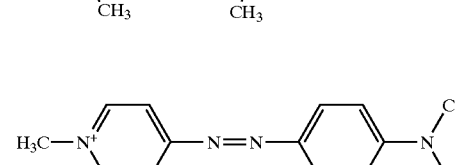 (I30)
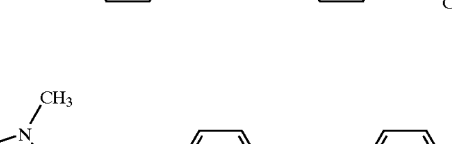 (I31)
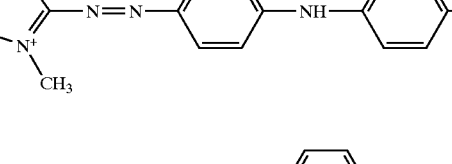 (I32)
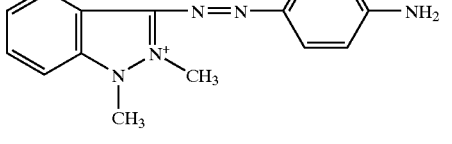 (I33)

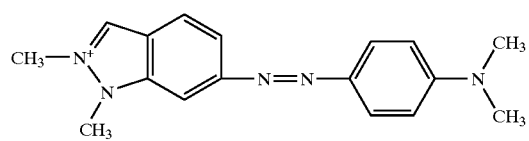 (I34)
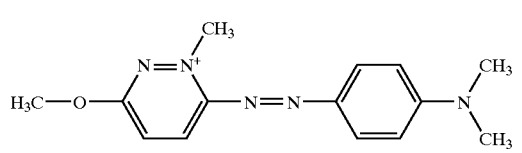 (I35)
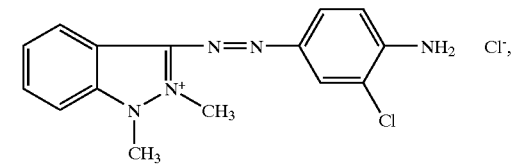 (I36)
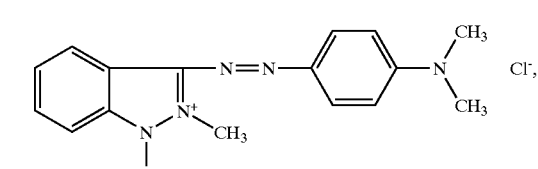 (I37)
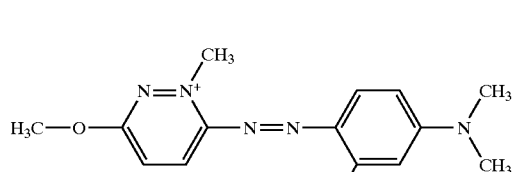 (I38)
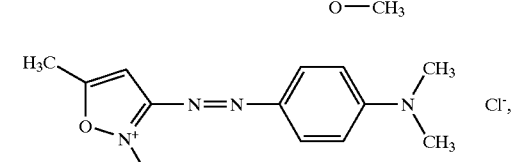 (I39)
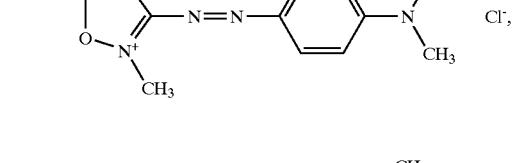 (I40)
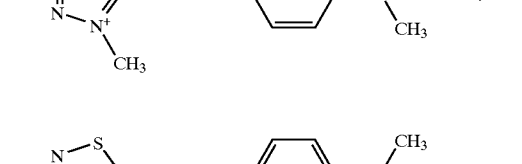 (I41)
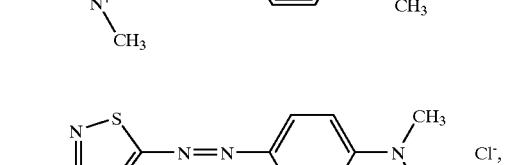 (I42)
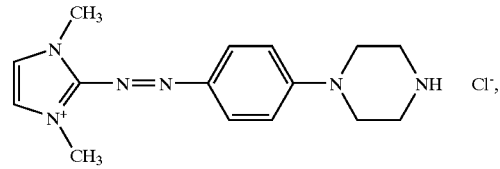 (I43)
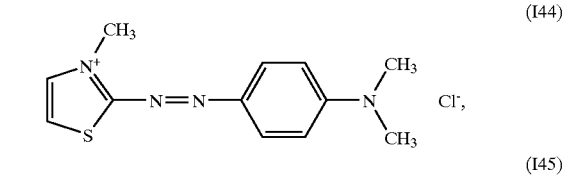 (I44)
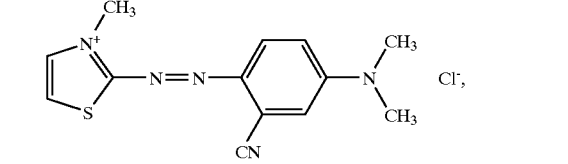 (I45)
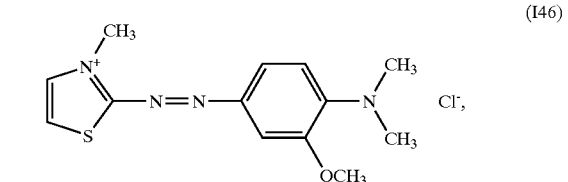 (I46)
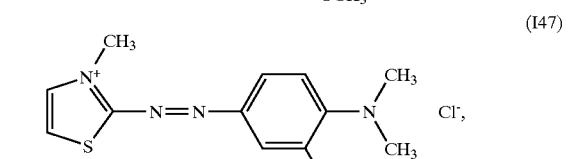 (I47)
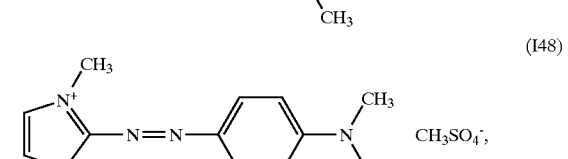 (I48)
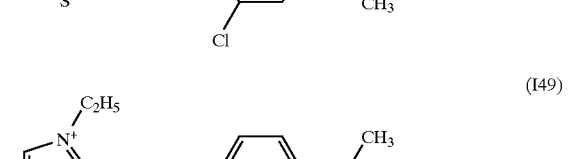 (I49)
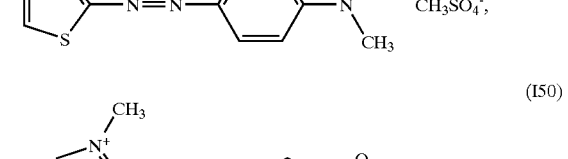 (I50)
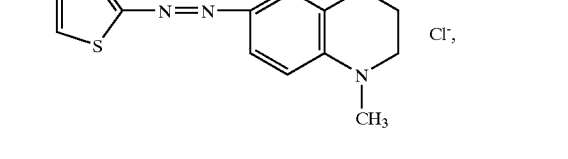 (I51)

5. The composition according to claim 1, wherein said at least one cationic direct dye of formula (II) is chosen from compounds of structures (II1) to (II12) below:

6. The composition according to claim 1, wherein said at least one cationic direct dye of formula (III) is chosen from compounds of structures (III1) to (III18) below:

-continued

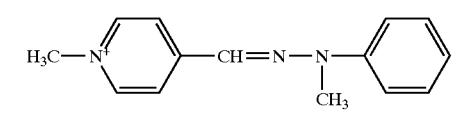   (III4)

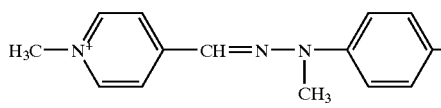   (III5)

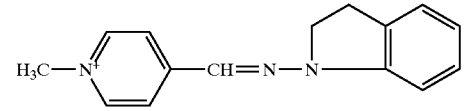   (III6)

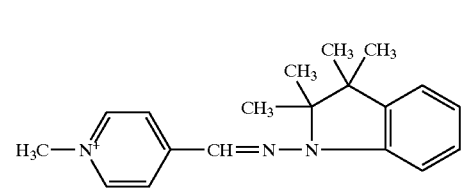   (III7)

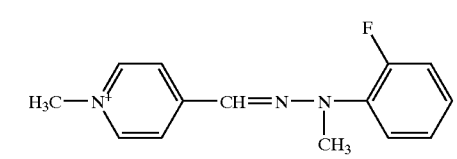   (III8)

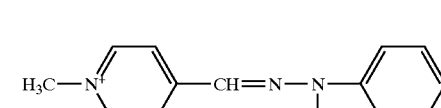   (III9)

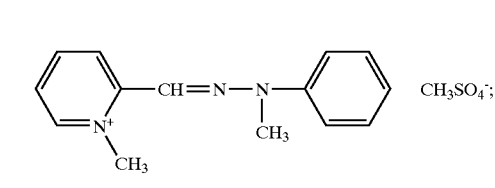   (III10)

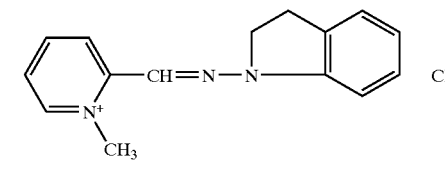   (III11)

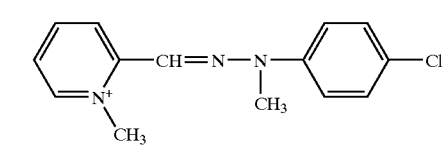   (III12)

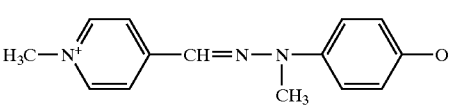   (III13)

-continued

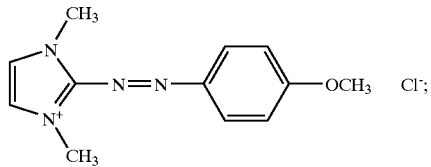   (III14)

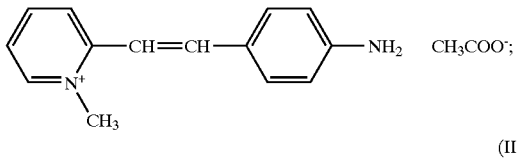   (III15)

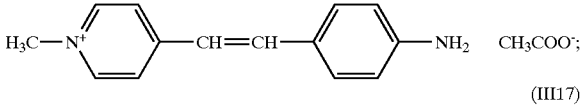   (III16)

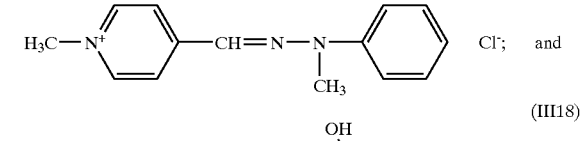   (III17)

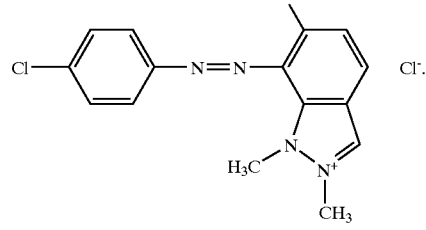   (III18)

7. The composition according to claim 1 wherein said at least one cationic direct dye of formula (IIII') is chosen from compounds of structures to structures (III'1) to (III'3) below:

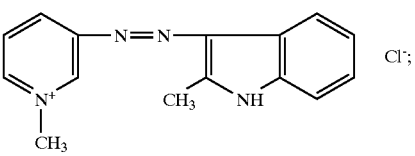   (III'1)

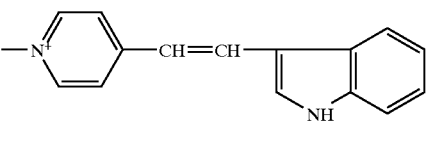   (III'2)

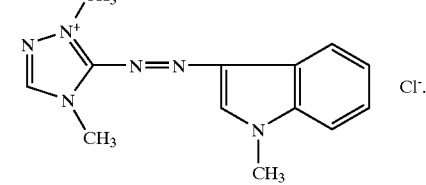   (III'3)

8. The composition according to claim 1, wherein said at least one cationic direct dye is present in an amount ranging from 0.001 to 10% by weight relative to the total weight of the composition.

9. The composition according to claim 2, wherein said at least one cationic direct dye is present in an amount ranging from 0.05 to 5% by weight relative to the total weight of the composition.

10. The composition according to claim 1, wherein said at least one nitrobenzene direct dye is chosen from compounds of formula (IV) below:

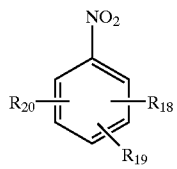

(IV)

in which:
  $R_{18}$ is chosen from amino radicals which are unsubstituted or are monosubstituted or disubstituted with a $C_1$–$C_4$ alkyl, $C_1$–$C_4$ monohydroxyalkyl, $C_2$–$C_4$ polyhydroxyalkyl, $C_1$–$C_4$ aminoalkyl, mono($C_1$–$C_4$) alkylamino($C_1$–$C_4$)alkyl, di($C_1$–$C_4$)alkylamino ($C_1$–$C_4$)alkyl, ureido($C_1$–$C_4$)alkyl or aryl radical or with an aryl radical in which the aryl ring is substituted with at least one radical chosen from hydroxyl, carboxyl, amino and di($C_1$–$C_4$)alkylamino radicals,
  $R_{19}$ is chosen from a hydrogen atom; a hydroxyl radical; amino radicals; $C_1$–$C_4$ alkyl radicals; $C_1$–$C_4$ alkoxy radicals; $C_1$–$C_4$ monohydroxyalkyl radicals; $C_2$–$C_4$ polyhydroxyalkyl radicals; $C_1$–$C_4$ monohydroxyalkoxy radicals; $C_2$–$C_4$ polyhydroxyalkoxy radicals; $C_1$–$C_4$ aminoalkoxy radicals; and amino radicals monosubstituted or disubstituted with a $C_1$–$C_4$ alkyl, $C_1$–$C_4$ monohydroxyalkyl, $C_2$–$C_4$ polyhydroxyalkyl, $C_1$–$C_4$ aminoalkyl, mono($C_1$–$C_4$)-alkylamino($C_1$–$C_4$) alkyl, di($C_1$–$C_4$)alkylamino($C_1$–$C_4$)alkyl, ureido ($C_1$–$C_4$)alkyl or aryl radical or with an aryl radical in which the aryl ring is substituted with one or more hydroxyl, carboxyl, amino or di($C_1$–$C_4$)alkylamino radicals; and
  $R_{20}$ is chosen from a hydrogen atom, halogen atoms, $C_1$–$C_4$ alkyl radicals, and nitro groups.

11. The composition according to claim 10, wherein said at least one nitrobenzene dye of formula (IV) is chosen from:
  2-amino-4-methyl-5-N-(β-hydroxyethyl)aminonitrobenzene,
  4-N-(β-ureidoethyl)aminonitrobenzene,
  4-(N-ethyl-N-β-hydroxyethyl)amino-1-N-(β-hydroxyethyl)aminonitrobenzene,
  2-N-(β-hydroxyethyl)amino-5-methylnitrobenzene,
  5-chloro-3-N-(ethyl)amino-4-hydroxynitrobenzene,
  5-amino-3-chloro-4-hydroxynitrobenzene,
  2-N-(γ-hydroxypropyl)amino-5-N,N-bis(β-hydroxyethyl)aminonitrobenzene,
  5-hydroxy-2-N-(γ-hydroxypropyl)aminonitrobenzene,
  1,3-bis(β-hydroxyethyl)amino-4-chloro-6-nitrobenzene,
  2,4-diaminonitrobenzene,
  3,4-diaminonitrobenzene,
  2,5-diaminonitrobenzene,
  3-amino-4-hydroxynitrobenzene,
  4-amino-3-hydroxynitrobenzene,
  5-amino-2-hydroxynitrobenzene,
  2-amino-5-hydroxynitrobenzene,
  4-amino-3-hydroxynitrobenzene,
  5-amino-2-hydroxynitrobenzene,
  2-amino-3-hydroxynitrobenzene,
  2-amino-5-N-(β-hydroxyethyl)aminonitrobenzene,
  2-amino-5-N,N-bis(β-hydroxyethyl)aminonitrobenzene,
  2,5-N,N'-(β-hydroxyethyl)aminonitrobenzene,
  2-N-(β-hydroxyethyl)amino-5-N,N-bis(β-hydroxyethyl)aminonitrobenzene,
  2-amino-5-N-(methyl)aminonitrobenzene,
  2-N-(methyl)amino-5-N, N-bis(β-hydroxyethyl)aminonitrobenzene,
  2-N-(methyl)amino-5-(N-methyl-N-β-hydroxyethyl)aminonitrobenzene,
  2,5-N,N'-(β-hydroxyethyl)aminonitrobenzene,
  2-N-(β-hydroxyethyl)amino-5-hydroxynitrobenzene,
  3-methoxy-4-N-(β-hydroxyethyl)aminonitrobenzene,
  2-N-(methyl)amino-4-β-hydroxyethyloxynitrobenzene,
  2-amino-3-methylnitrobenzene,
  2-N-(β-hydroxyethyl)amino-5-aminonitrobenzene,
  2-amino-4-chloro-5-N-(β-hydroxyethyl)aminonitrobenzene,
  2-amino-4-methyl-5-N-(β-hydroxyethyl)aminonitrobenzene,
  2-amino-4-methyl-5-N-(methyl)aminonitrobenzene,
  2-N-(β-hydroxyethyl)amino-5-methoxynitrobenzene,
  2-amino-5-β-hydroxyethyloxynitrobenzene,
  2-N-(β-hydroxyethyl)aminonitrobenzene,
  3-amino-4-N-(β-hydroxyethyl)aminonitrobenzene,
  3-β-hydroxyethyloxy-4-N-(β-hydroxyethyl)aminonitrobenzene,
  2-N-(methyl)amino-4-β,γ-dihydroxypropyloxynitrobenzene,
  2-N-(β-hydroxyethyl)amino-5-β-hydroxyethyloxynitrobenzene,
  2-N-(β-hydroxyethyl)amino-5-β,γ-dihydroxypropyloxynitrobenzene,
  2-hydroxy-4-N-(β-hydroxyethyl)aminonitrobenzene,
  2-N-(methyl)amino-4-methyl-5-aminonitrobenzene,
  2-amino-4-isopropyl-5-N-(methyl)aminonitrobenzene,
  2-N-(methyl)amino-5-(N-methyl-N-β,γ-dihydroxypropyl)aminonitrobenzene,
  3-N-(β-hydroxyethyl)amino-4-N-(β-hydroxyethyl)aminonitrobenzene,
  2-amino-4-methyl-5-N-(β,γ-dihydroxypropyl)aminonitrobenzene,
  2-amino-4-methyl-5-hydroxynitrobenzene,
  2-N-(β-hydroxyethyl)amino-4-N-(β-hydroxyethyl)aminonitrobenzene,
  2-amino-5-N-(β-aminoethyl)aminonitrobenzene,
  2-N-(β-aminoethyl)amino-5-methoxynitrobenzene,
  2-N-(methyl)amino-5-N-(β-aminoethyl)aminonitrobenzene,
  2-N-(β-aminoethyl)amino-4-N,N-(dimethyl)aminonitrobenzene,
  3-amino-4-N-(β-aminoethyl)aminonitrobenzene,
  2-amino-4-methyl-5-N-(β-aminoethyl)aminonitrobenzene,
  2-N-(β-aminoethyl)amino-5-N N-bis(β-hydroxyethyl)aminonitrobenzene, 3-β-aminoethyloxy-4-aminonitrobenzene,
2-N-(methyl)amino-5-(N-δ-amino-n-butyl)aminonitrobenzene,
2-N-(γ-amino-n-propyl)amino-5-N,N-(dimethyl)aminonitrobenzene,
3-methoxy-4-N-(β-aminoethyl)aminonitrobenzene, 2-N-(β-aminoethyl)amino-5-aminonitrobenzene,
2-amino-4-chloro-5-N-(β-aminoethyl)aminonitrobenzene,
2-N-(β-aminoethyl)amino-4-methoxynitrobenzene,
2-N-(β-aminoethyl)aminonitrobenzene,
2-N-(β-aminoethyl)amino-5-N-(β-aminoethyl)aminonitrobenzene,
2-N-(β-aminoethyl)amino-4-β-hydroxyethyloxynitrobenzene,
3-β-hydroxyethyloxy-4-N-(β-aminoethyl)aminonitrobenzene,
2-amino-5-aminoethyloxynitrobenzene,
3-hydroxy-4-N-(β-aminoethyl)aminonitrobenzene,
2-N-(β-aminoethyl)amino-5-β-hydroxyethyloxynitrobenzene,
2-N-(β-aminoethyl)amino-4-hydroxynitrobenzene,
2-{[2-hydroxy-3-N-(β-hydroxyethyl)amino-6-nitro]benzyloxy}ethylamine, and
2-{[2-hydroxy-3-N-(β-hydroxypropyl)amino-6-nitro]benzyloxy}ethylamine.

12. The composition according to claim 11, wherein said at least one nitrobenzene dye of formula (IV) is chosen from:
2-amino-4-methyl-5-N-(β-hydroxyethyl)aminonitrobenzene,
4-N-(β-ureidoethyl)aminonitrobenzene,
4-(N-ethyl-N-β-hydroxyethyl)amino-1-N-(β-hydroxyethyl)aminonitrobenzene,
2-N-(β-hydroxyethyl)amino-5-methylnitrobenzene,
5-chloro-3-N-(ethyl)amino-4-hydroxynitrobenzene,
5-amino-3-chloro-4-hydroxynitrobenzene,
2-N-(γ-hydroxypropyl)amino-5-N, N-bis(β-hydroxyethyl)aminonitrobenzene,
5-hydroxy-2-N-(γ-hydroxypropyl)aminonitrobenzene,
1,3-bis(β-hydroxyethyl)amino-4-chloro-6-nitrobenzene,
3,4-diaminonitrobenzene,
2-amino-5-hydroxynitrobenzene,
2-amino-3-hydroxynitrobenzene,
2-amino-5-N-(β-hydroxyethyl)aminonitrobenzene,
2-amino-5-N,N-bis(β-hydroxyethyl)aminonitrobenzene,
2-N-(β-hydroxyethyl)amino-5-N,N-bis(β-hydroxyethyl)aminonitrobenzene,
2-N-(β-hydroxyethyl)amino-5-hydroxynitrobenzene,
2-N-(β-hydroxyethyl)amino-5-aminonitrobenzene,
2-N-(β-aminoethyl)amino-4-methoxynitrobenzene, and
2-N-(β-aminoethyl)amino-5-β-hydroxyethyloxynitrobenzene.

13. The composition according to claim 1, wherein said at least one nitrobenzene dye is present in an amount ranging from 0.0005 to 15% by weight of said composition.

14. The composition according to claim 13, wherein said at least one nitrobenzene dye is present in an amount ranging from 0.005 to 10% by weight of said composition.

15. The composition according to claim 1 wherein said composition further comprises at least one additional component chosen from oxidation bases and couplers, said oxidation bases being chosen from para-phenylenediamines, para-aminophenols, orthophylenediamines, heterocyclic bases and acid-addition salts thereof, and said couplers being chosen from meta-phenylenediamines, meta-aminophenols, meta-diphenols, heterocyclic couplers, and acid-addition salts thereof.

16. The composition according to claim 15 wherein said heterocyclic couplers are chosen from indole compounds, indoline compounds benzimidazole compounds, benzomorpholine compounds, sesamol compounds, pyridine compounds, pyrimidine compounds, pyrazole compounds, and acid-addition salts thereof.

17. The composition according to claim 15, wherein said at least one oxidation base is present in the composition in an amount ranging from 0.0005 to 12% by weight relative to the total weight of the composition and said at least one coupler is present in an amount ranging from 0.0001 to 10% by weight relative to the total weight of the composition.

18. The composition according to claim 17, wherein said at least one oxidation base is present in the composition in an amount ranging from 0.005 to 8% by weight relative to the total weight of the composition and said at least one coupler is present in an amount ranging from 0.005 to 5% by weight relative to the total weight of the composition.

19. The composition according to claim 15, wherein said acid-addition salts are chosen from hydrochlorides, hydrobromides, sulphates, tartrates, lactates and acetates.

20. The composition according to claim 15, wherein said composition further comprises at least one oxidizing agent.

21. The composition according to claim 20, wherein said at least one oxidizing agent is chosen from hydrogen peroxide, urea peroxide, alkali metal bromates, persalts, and enzymes.

22. The composition according to claim 21, wherein said enzymes are chosen from peroxidases and two-electron oxidoreductases.

23. The composition according to claim 22, wherein said two-electron oxidoreductases are chosen from pyranose oxidases, glucose oxidases, glycerol oxidases, lactate oxidases, pyruvate oxidases and uricases.

24. The composition according to claim 22 wherein said two-electron oxidoreductases are chosen from uricases of animal, microbiological and biotechnological origin.

25. The composition according to claim 22, wherein said two-electron oxidoreductases are present in said composition in an amount ranging from 0.01 to 20% by weight relative to the total weight of the composition.

26. The composition according to claim 25, wherein said two-electron oxidoreductases are present in said composition in an amount ranging from 0.1 to 5% by weight relative to the total weight of the composition.

27. The composition according to claim 24, wherein said composition further comprises a donor for said 2-electron oxidoreductases, wherein said donor is chosen from uric acid and its salts.

28. The composition according to claim 20 wherein said persalts are chosen from perborates and persulphates.

29. The composition according to claim 1, further comprising water or a mixture of water and at least one organic solvent.

30. The composition according to claim 1, wherein said composition has a pH ranging from 5 to 11.

31. A process for dyeing keratin fibers, comprising:
separately storing a first composition;
separately storing a second composition;
mixing said first composition with said second composition;

applying said mixture to said fibers; and, developing for a period of time sufficient to achieve a desired coloration, wherein said first composition comprises a ready-to-use composition according to claim 1 and an additional ingredient chosen from oxidation bases and couplers, and wherein said second composition comprises at least one oxidizing agent.

32. A multi-compartment dyeing kit, comprising at least two separate compartments, wherein a first compartment contains a first composition comprising a ready-to-use composition for dyeing keratin fibers according to claim 1, and an additional ingredient chosen from oxidation bases and couplers, and a second compartment contains a second composition comprising at least one oxidizing agent.

33. A process for dyeing keratin fibers, comprising applying at least one ready-to-use composition for the oxidation dyeing of keratin fibers to said fibers for a period of time sufficient to develop a desired coloration, wherein said ready-to-use dye composition comprises:

at least one nitrobenzene direct dye; and, at least one cationic direct dye chosen from:

(a) compounds of formula (I), below:

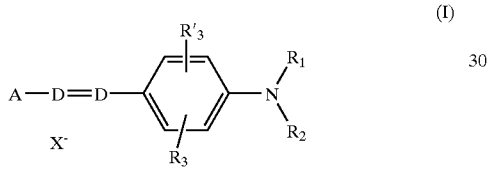

(I)

wherein:

$X^-$ is an anion;

$R_1$ and $R_2$, which may be identical or different, are chosen from a hydrogen atom, a 4'-aminophenyl radical, and $C_1$–$C_4$ alkyl radicals which can be substituted with a —CN, —CH or —NH$_2$ radical, or form, with a carbon atom of the benzene ring, an optionally oxygenated or nitrogenous heterocycle which can be substituted with one or more $C_1$–$C_4$ alkyl radicals;

$R_3$ and $R'_3$, which may be identical or different, are chosen from a hydrogen atom, halogen atoms chosen from chlorine, bromine, iodine and fluorine, cyano radicals, $C_1$–$C_4$ alkoxy radicals, and acetyloxy radicals;

D is chosen from a nitrogen atom and a —CH group;

A is chosen from structures A1 to A19, below:

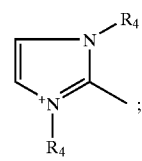

A₁

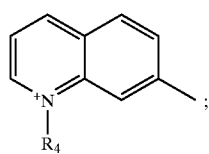

A₂

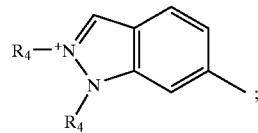

A₃

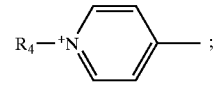

A₄

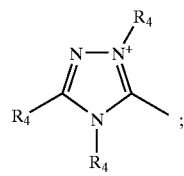

A₅

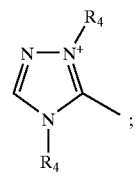

A₆

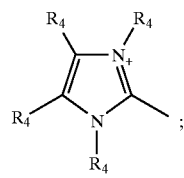

A₇

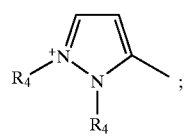

A₈

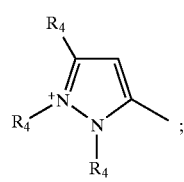

A₉

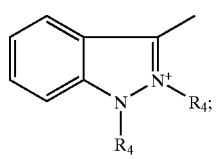

A₁₀

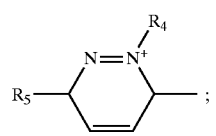

A₁₁

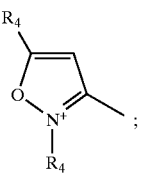

A₁₂

-continued

A13: [pyridinium with R4 on N+]

A14: [thiazolium with R4 on N+]

A15: [thiadiazolium with R4 on N+]

A16: [thiadiazolium variant with R4]

A17: [thiadiazole with two R4]

A18: [indazole with two R4]

and

A19: [imidazolium with two R4]

wherein R$_4$ is chosen from C$_1$–C$_4$ alkyl radicals which can be substituted with a hydroxyl radical and R$_5$ is chosen from C$_1$–C$_4$ alkoxy radicals, and further wherein when D is a —CH group, when A is A$_4$ or A$_{13}$, and when R$_3$ is other than an alkoxy radical, then R$_1$ and R$_2$ are not simultaneously a hydrogen atom, and further wherein when D is a nitrogen atom, A is chosen from A$_1$–A$_{12}$ and A$_{14}$–A$_{19}$;

(b) compounds of formula (II), below:

(II)

B—N=N—[phenyl with R$_8$, R$_9$ on ring and N(R$_6$)(R$_7$)]  X$^-$ wherein:

R$_6$ is chosen from a hydrogen atom and C$_1$–C$_4$ alkyl radicals;

R$_7$ is chosen from a hydrogen atom, alkyl radicals which can be substituted with a —CN radical or with an amino group, and a 4'-aminophenyl radical, or forms, with R$_6$, a heterocycle, which can be oxygenated or nitrogenous, and which can be substituted with at least one C$_1$–C$_4$ alkyl radical;

R$_8$ and R$_9$, which may be identical or different, are chosen from a hydrogen atom, halogen atoms, C$_1$–C$_4$ alkyl radicals, C$_1$–C$_4$ alkoxy radicals, and a —CN radical;

X$^-$ is an anion;

B is chosen from structures B1 to B6, below:

B1: [thiazolium with R$_{10}$ groups]

B2: [thiadiazolium with R$_{10}$ groups]

B3: [thiadiazolium with R$_{10}$, R$_{11}$, R$_{12}$, N substituent]

B4: [quinolinium with R$_{10}$]

B5: [quinolinium variant with R$_{10}$]

and

B6: [isothiazolium with R$_{10}$ groups]

wherein:

R$_{10}$ is chosen from C$_1$–C$_4$ alkyl radicals;

R$_{11}$ and R$_{12}$, which may be identical or different, are chosen from a hydrogen atom and C$_1$–C$_4$ alkyl radicals;

(c) compounds of formula (III) and compounds of formula (III') below:

(III)

E—D$_1$=D$_2$—(N)$_m$—[phenyl with R$_{14}$, R$_{13}$, R$_{15}$]  X$^-$

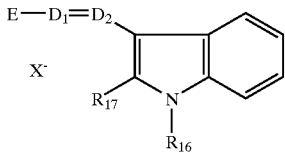
(III')

wherein $R_{13}$ is chosen from a hydrogen atom, $C_1$–$C_4$ alkoxy radicals, halogen atoms, and amino radicals;

$R_{14}$ is chosen from a hydrogen atom and $C_1$–$C_4$ alkyl radicals, or forms, with a carbon atom of the benzene ring, a heterocycle which is optionally oxygenated and which can be substituted with at least one $C_1$–$C_4$ alkyl group, $R_{15}$ is chosen from a hydrogen atom and halogen atoms;

$R_{16}$ and $R_{17}$, which may be identical or different, are chosen from a hydrogen atom and $C_1$–$C_4$ alkyl radicals;

$D_1$ and $D_2$, which may be identical or different, are chosen from a nitrogen atom and a —CH group;

$X^-$ is an anion;

m=0 or 1, wherein when $R_{13}$ is an unsubstituted amino group, then $D_1$ and $D_2$ simultaneously are a —CH group and m=0; and E is chosen from structures E1 to E8 below:

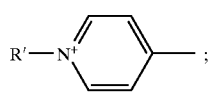
E1

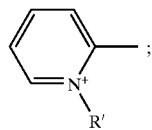
E2

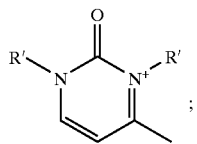
E3

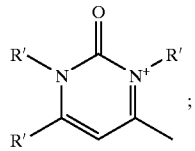
E4

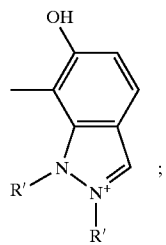
E5

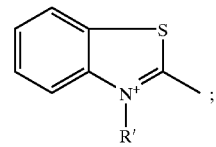
E6

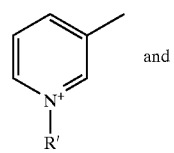
and
E7

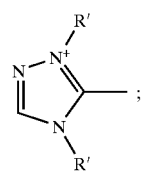
E8 and with the proviso that when m=0 and $D_1$ is a nitrogen atom, then E can also be chosen from E9 below:

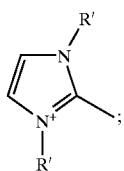
E9 wherein R' for structures E1 to E9 is chosen from $C_1$–$C_4$ alkyl radicals, and with the further proviso that in said compounds of formula (III) when $D_1$ and $D_2$ are simultaneously a nitrogen atom, m=0, $R_{13}$ is an amino radical and $R_{15}$ is a hydrogen atom, then E is chosen from $E_1$, $E_3$ to $E_5$, $E_7$ and $E_8$.

* * * * *

UNITED STATES PATENT AND TRADEMARK OFFICE
CERTIFICATE OF CORRECTION

PATENT NO. : 6,712,861 B2
DATED : March 30, 2004
INVENTOR(S) : Christine Rondeau It is certified that error appears in the above-identified patent and that said Letters Patent is hereby corrected as shown below:

Column 22,
Line 27, "X is" should read -- $X^-$ is --.
Line 38, "atom halogen" should read -- atom, halogen --.

Column 27,
Line 22, "claim 1 wherein" should read -- claim 1, wherein --.

Column 36,
Line 37, "claim 1 wherein" should read -- claim 1, wherein --.
Line 39, "structures to structures (III'1)" should read -- structures (III'1) --.

Column 37,
Line 57, "5-hydroxy-2-N-(y-hydroxypropyl)aminonitrobenzene," should read
-- 5-hydroxy-2-N-(γ-hydroxypropyl)aminonitrobenzene, --.

Column 38,
Lines 11-12, "2-N-(methyl)amino-5-N, N-bis(β-hydroxyethyl)aminonitrobenzene," should read -- 2-N-(methyl)amino-5-N,N-bis(β-hydroxyethyl)aminonitrobenzene, --
Lines 66-67, "2-N-(β-aminoethyl)amino-5-N N-bis(β-hydroxyethyl)aminonitrobenzene," should read -- 2-N-(β-aminoethyl)amino-5-N,N-bis(β-hydroxyethyl)aminonitrobenzene, --.

Column 39,
Lines 4-5, "2-N-(y-amino-n-propyl)amino-5-N,N-(dimethyl)aminonitrobenzene," should read -- 2-N-(γ-amino-n-propyl)amino-5-N,N-(dimethyl)aminonitrobenzene, --.
Lines 41-42, "2-N-(γ-hydroxypropyl)amino-5-N, N-bis(β-hydroxyethyl)aminonitrobenzene," should read -- 2-N-(γ-hydroxypropyl)amino-5-N,N-bis(β-hydroxyethyl)aminonitrobenzene, --.

Column 40,
Line 3, "bases and" should read -- bases, and --.
Line 9, "compounds benzimidazole" should read -- compounds, benzimidazole --.
Line 56, "claim 20" should read -- claim 21 --.

UNITED STATES PATENT AND TRADEMARK OFFICE
CERTIFICATE OF CORRECTION

PATENT NO.    : 6,712,861 B2
DATED         : March 30, 2004
INVENTOR(S)   : Christine Rondeau It is certified that error appears in the above-identified patent and that said Letters Patent is hereby corrected as shown below:

Column 41,
Line 42, "-CH or" should read -- -OH or --.

Signed and Sealed this

Third Day of August, 2004

JON W. DUDAS
*Acting Director of the United States Patent and Trademark Office*